United States Patent
Fukushima et al.

(10) Patent No.: US 6,702,757 B2
(45) Date of Patent: Mar. 9, 2004

(54) NON-INVASIVE BRAIN FUNCTION EXAMINATION

(75) Inventors: Shogo Fukushima, Moriguchi (JP); Shuji Murakami, Takaishi (JP); Kenshi Suzuki, Osaka (JP); Ryoji Nakajima, Hirakata (JP)

(73) Assignee: Matsushita Electric Works, Ltd., Kadoma (JP)

( * ) Notice: Subject to any disclaimer, the term of this patent is extended or adjusted under 35 U.S.C. 154(b) by 0 days.

(21) Appl. No.: 10/026,646

(22) Filed: Dec. 27, 2001

(65) Prior Publication Data

US 2002/0099305 A1 Jul. 25, 2002

(30) Foreign Application Priority Data

Dec. 28, 2000 (JP) .......................................... 2000-402816

(51) Int. Cl.⁷ .............................................. A61B 13/00
(52) U.S. Cl. ...................................................... 600/558
(58) Field of Search ............................ 600/558; 706/16, 706/23; 250/221; 351/210, 212, 211, 246, 209; 348/333.03, 221.1, 240.3, 333.1, 375; 345/8, 9; 396/51

(56) References Cited

U.S. PATENT DOCUMENTS

| | | | |
|---|---|---|---|
| 5,319,398 A | * | 6/1994 | Weijland .................... 351/212 |
| 5,422,690 A | | 6/1995 | Rothberg et al. |
| 5,649,061 A | * | 7/1997 | Smyth ......................... 706/16 |
| 5,913,310 A | | 6/1999 | Brown |
| 6,102,870 A | | 8/2000 | Edwards |
| 6,120,461 A | * | 9/2000 | Smyth ........................ 600/558 |
| 6,162,186 A | | 12/2000 | Scinto et al. |
| 6,307,589 B1 | * | 10/2001 | Maquire, Jr. .......... 348/333.03 |

FOREIGN PATENT DOCUMENTS

| | | |
|---|---|---|
| CA | 2209886 | 1/1998 |
| WO | WO 98/57579 | 12/1998 |

OTHER PUBLICATIONS

K.L. Lueck, et al., Neuropsychiatry, Neuropsychology and Behavioral Neurology, vol. 13, No. 2, pp. 77–82, "Eye Movement Abnormalities During Reading in Patients With Alzheimer Disease", 2000 (pp. 78, 80 and 82 will be filed later).

S. Murakami, et al., Alzheimer's and Parkinson'Diseases, pp. 13–17, "Stereopsis in Alzheimer'Disease: Measuring Binocular Eye Movement", 1995.

R. Prettyman, et al., Journal of Neurology, Neurosurgery, and Psychiatry, vol 62, pp. 665–668, "Altered Pupillary Size And Darkness and Light Reflexes in Alzheimer'Disease", 1997.

(List continued on next page.)

Primary Examiner—Max F. Hindenburg
Assistant Examiner—Brian Szmal
(74) Attorney, Agent, or Firm—Oblon, Spivak, McClelland, Maier & Neustadt, P.C.

(57) ABSTRACT

An apparatus for examining a subject's brain functions acquires two or more indexes of pupillary indexes that show the subject's pupillary characteristics, visual indexes that show the subject's visual system functions, intelligence evaluating indexes that are results of the an intelligence test carried out on the subject, and behavior evaluating indexes that show the results the subject's behavior examination. Two or more indexes are stored in a memory and outputted from an output unit. By combining two or more kinds of independent indexes, accurate determination of dementia cases and further the degree of senescence of brain functions can be achieved. In addition, the brain function examining apparatus puts together a number of a plurality of indexes by the multivariate calculation and converts the indexes into different values of fewer numbers.

25 Claims, 23 Drawing Sheets

OTHER PUBLICATIONS

E. Rösler, et al., Neuropsychology, vol. 14, No. 3, pp. 398–408, "Alterations of Visual Search Strategy in Alzheimer'Disease and Aging", 2000 (pp. 399 will be filed later).

L.F.M. Scinto, et al., Arch. Neurol, vol. 51, pp. 682–688, "Impairment of Spatially Directed Attention in Patients With Probable Alzheimer's Disease as Measured By Eye Movements", Jul. 1994 (pp. 683, 685 and 687 will be filed later).

G.L. Trick, et al., Neurology, vol. 41, pp. 1437–1439, "Visual Sensitivity to Motion: Age–Related Changes and Deficits in Senile Dementia of the Alzheimer Type", Sep. 1991 (pp. 1438 and 1440 will be filed later).

G. Zaccara, et al., Journal of Neurological Sciences, vol. 112, pp. 81–89, "Smooth–Pursuit Eye Movements: Alterations In Alzheimer's Disease", 1992.

A. Moser, et al., Original Research Article, vol. 6, pp. 264–268, XP–008002167, "Eye Movement Dysfunction In Dementia of The Alzheimer Type", 1995.

U.S. patent application Ser. No. 09/693,898, filed Oct. 23, 2000, pending.

U.S. patent application Ser. No. 10/026,646, filed Dec. 27, 2001, pending.

* cited by examiner

Fig.5
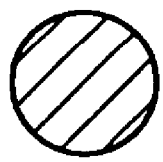
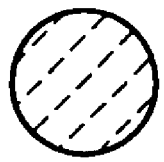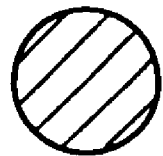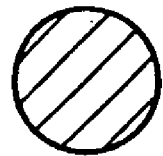
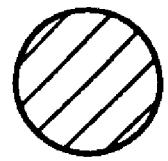

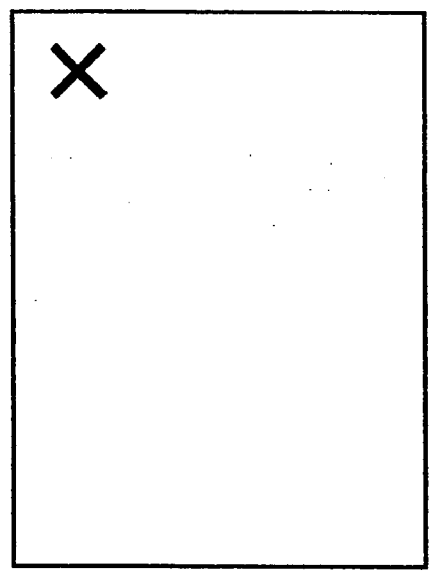
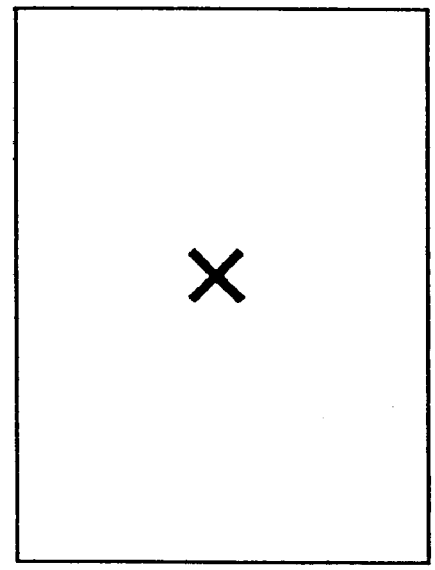
Fig. 18

Fig. 23 dkagjpoawitjaejfaekdfaerja
ijkdajhifijshijmiraarmk5fkj
jdjijhfshpwrwqpaprjkflvm
fkjagprpjihhgvjpsrgkfssjbsj
kdsjgkjshiugpeshkgjhsdpeq

NON-INVASIVE BRAIN FUNCTION EXAMINATION

BACKGROUND OF THE INVENTION

1. Field of the Invention

The present invention relates to a brain function examination by the utilization of a pupillary light reflex, eye movement, neuro-psychological test and behavior evaluation. More specifically, the present invention relates to a brain function examining apparatus and a method therefore, wherein indexes such as the pupillary light reflex and eye movements exhibited by a subject is detected to determine a brain disorder such as, for example, the degree of senescence of the brain, disorder of the autonomic nervous system, the dementia, Meniere disease, vertigo or the like.

2. Description of the Prior Art

It is generally said that the size of a pupil decreases with age (for example, Ishikawa, et al., "Fukyuu-gata Denshi Doukoukei Irisukohda (C-2514) (Neuro Ophthalmology), Vol. 10, No.2, pp. 106–110, 1993). The smooth muscle that adjusts the size of the pupil is governed by the autonomic nervous system and the size of the pupil and/or the pupillary change reflect the degree of activity of the autonomic nervous system.

It is also pointed out that the pupil is associated with the Alzheimer's disease which is generally considered closely associated with the brain function. L. F. M. Scinto, et al. have reported that by measuring the rate of dilation of the pupil before and after a dilating agent is instillated, diagnosis of the Alzheimer's disease which is considered one of dementia is possible ("A Potential Noninvasive Neurobiological Test for Alzheimer's Disease", Science, 266, pp. 1051–1054, 1994). According to this method (hereinafter referred to as an instillation method), since diagnosis of the Alzheimer's disease is done in reference to the rate of dilation of the pupil, the result of such diagnosis is subjective. In this respect, it may be said that the instillation method is more excellent than the interview-based medical examination which tends to result in subjective results. Determination based on the interview-based medical examination includes, for example, The Revised version of Hasegawa Dementia Scale (HDSR) which has hitherto been used in diagnosing dementia. It is noted that measurement of the pupil based on the installation method requires 30 minutes and cannot be applied to some of subjects suffering from ophthalmic diseases. Furthermore, reliability of the eye drop test is controversial recently.

To overcome the above discussed inconveniences, a diagnosis technique is available in which the characteristic of the pupil (the pupillary light reflex) is measured to determine if dementia is apparent. This is based on researcher's report that the normal and dementia cases exhibit different pupillary light reflexes (Shi, et al., "A Study for Objective Measurement of the Senile Dementia by Light-Reflex", Iyou Densi to Seitai Kougaku (Medical Electronics and Bio-engineering), Vol. 36, No. 3, pp. 210–214, 1998). According to this diagnosing method, unlike the installation method, measurement of the pupillary light reflex completes in a short time and has an advantage that the measurement brings no side-effect.

However, according to the Shi, et al. report, the normal and dementia cases are merely compared with each other by calculating predetermined indexes (pupillary constricting rate, pupillary constricting time and pupillary redilating rate) indicative of the pupillary light reflex. Accordingly, it is not possible to output (display), for example, a subject index and an average index for the dementia cases and then to utilize a relative relationship displayed in determining if the subject is suffering from dementia or the like. Also, since the pupillary light reflex varies from person to person as is the case with physiological indexes, it cannot be said that with only the three indexes reported by Shi, et al. the manner of pupillary change is sufficiently grasped. Accordingly, determination of the dementia, the degree of autonomic activity, the degree of senescence of the brain function or the like with the use of such small indexes lacks reliability.

Furthermore, even if a large number of the indexes representative of the pupillary lights reflex are used, there are cases in which deviation is generated in the results due to individual differences. More generally, using only one type of physiological index may generate deviations in the results due to individual differences. With this, it is unable to meet the requirements of the persons concerned for further improving the reliability of determination.

SUMMARY OF THE INVENTION

It is an object of the present invention to examine brain functions at higher accuracy by combining various independent indexes (pupillary light reflex index for reflecting the degree of activity of the autonomic nervous system, visual system functional index concerning oculogyration for reflecting the degree of activity of visual cortex of brain, intelligence evaluating index that reflects the intelligence test of the subject, behavior evaluating index concerning the behavior of the subject, etc.).

It is another object of the present invention to put together the information on various independent indexes, convert them into another values with fewer indexes, and to examine brain functions more easily by using the converted values.

To achieve these objects, an apparatus which examines brain functions of a subject comprises two or more examining units, which are a pupillary change examining unit which examines characteristics of a pupil of the subject and which calculates a pupillary index, a visual system function examining unit which examines visual system functions of the subject and which calculates a visual index, an intelligence examining unit which carries out an intelligence test on the subject and which calculates an intelligence evaluating index, and a behavior examining unit which provides a behavior evaluating index that shows a result of behavior test of the subject. The apparatus further comprises a memory device which stores a plurality of indexes presented by the two or more examining units, and an output unit which outputs the plurality of indexes stored in the storage unit. The output unit sends data representing a plurality of indexes to, for example, a display and/or a printer.

The brain function examining apparatus according to the present invention further comprises a multivariate calculator which calculates at least one discriminant score in the quantity less than a number of input values based on a plurality of input values. The multivariate calculator calculates the at least one discriminant score using the plurality of indexes presented by the two or more examining units and the plurality of reference indexes accumulated in the database as the plurality of input values for calculating the at least one discriminant score.

According to the present application, it is possible to achieve the accurate determination of dementia, and further achieve the determination of degree of senescence of the brain function.

Other objects and attainments together with a fuller understanding of the invention will become apparent and appreciated by referring to the following description and claims taken in conjunction with the accompanying drawings.

BRIEF DESCRIPTION OF THE DRAWINGS

The above and further objects and features of the present invention will become more apparent from the following detailed description when the same is read in connection with the accompanying drawings wherein:

FIG. 5 is a diagram of an example of the image for examination;

FIG. 18 is a diagram of an example of the image for examination.

FIG. 23 is a exemplary diagram used for a task of searching letters.

DETAILED DESCRIPTION OF THE PREFERRED EMBODIMENTS

Figure 1A:
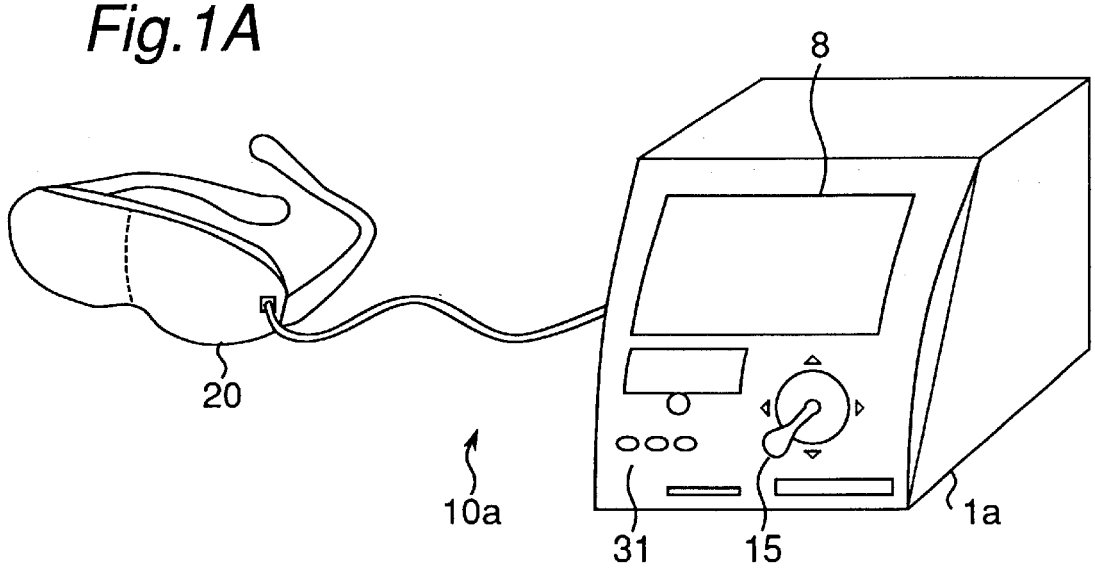
FIG. 1A is a diagram of the appearance of a brain function examining apparatus according to the present invention.

Referring now to accompanying drawings, preferred embodiments of the present invention will be described. In the drawings, like component elements that carry out like functions are given like reference characters.

First of all, prior to describing each preferred embodiment, the general configuration and functions of the brain function examining apparatus according to the present invention will be described.

FIG. 1A is a diagram of the appearance of brain function examining apparatus 10a. Brain function examining apparatus 10a includes a controller 1a and an imaging unit 20 shown as goggles connected to each other. Controller 1a is equipped with various input units 15, 31 utilized for collecting subject data, display section 8 for displaying examination results, etc., and others. Controller 1a is not necessarily limited to the form illustrated but may be a general-purpose personal computer (hereinafter called "PC"). Imaging unit 20 is an apparatus used by the subject by mounting it to its own head, and is utilized for examination of pupillary change and visual system functions by taking images of reactions of pupils or displaying images, etc. as described later. The data obtained is accumulated in the database (not shown) installed inside.

Imaging unit 20 has a head-mount display shape, and not only takes images of pupils of the subject but also projects images on the inside. Imaging unit 20 is provided separately from the controller but may be provided integral with controller 1a as part of controller 1a. By integrating the imaging unit into the controller, the subject does not need to move to a different room for receiving examinations, etc. of the visual system functions, and is able to continue examinations in the same controller 1a.

The brain function examining apparatus according to the present invention deduces plural types of physiological indexes concerning each subject, which are independent to each other, using imaging unit 20. "Physiological indexes" referred to here means indexes concerning the pupillary lights reflex that reflects the activity condition of the autonomic nervous system (hereinafter called the "pupillary index"), the index showing the characteristics concerning the visual functions that reflect the activity condition of visual cortex of the brain (hereinafter called the "visual index"), the index showing the results concerning the intelligence test on the subject (hereinafter called the "intelligence evaluating index"), the index showing the results concerning the activity evaluation of the subject obtained from asking questions to any third party other than the subject (for example, care providers of the relevant subject) and obtaining from their replies (hereinafter called the "behavior evaluating index"), etc. The brain function examining apparatus can output plural types of physiological indexes deduced and each index of a plurality of subjects measured in advance and accumulated in the database.

For example, in the brain function examining apparatus according to Embodiment 1, the pupillary index that indicates pupillary characteristics by the examination of autonomic nervous system is deduced, and in addition, examines the visual functions and deduces the visual index. Based on the results of both examinations, the apparatus examines the brain functions. Thus, doctors and the test personnel can easily and highly accurately determine the brain functions with high reliability. The "determination of brain functions" referred to herein means to determine whether the subject can be said healthy or not, or whether the subject may have a possibility of suffering from dementia (for example, Alzheimer's disease), senescence of brain functions, encephalopathy such as decrease of the activity of autonomic nervous system, etc., and furthermore, the determination of the degree of encephalopathy.

The grounds of deducing plural types of physiological indexes such as visual index and utilizing them for determining brain functions are supported by a plurality of scientific papers reporting that the healthy normal elderly and the dementia elderly can be distinguished by examining the visual functions which are independent from the autonomic nervous system. Examples of scientific papers include Reference 1: Cronin-Golomb Alice et al., "Visual Dysfunction in Alzheimer's Disease: Relation to Normal Aging." Ann Neurol 1991; 29; 41–52; Reference 2: G. Zaccara et al.: "Smooth-pursuit eye movements; alteration in Alzheimer's disease." J. Neurol. Sci. 1992; 112; 81–89; and Reference 3: Gray L. Trick et al.: "Visual sensitivity to motion: Age-related changes and deficits in senile dementia of the Alzheimer type." NEUROLOGY 1991; 41; 1437–1440. Based on this, as compared to the case in which the brain functions are examined only by one type of index, the statistical significance level value of the healthy normal elderly group and the dementia elderly group is reduced, the identification ratio or sensitivity of the dementia is improved, and furthermore, the degree of senescence of brain can be determined more accurately.

Figure 1B:
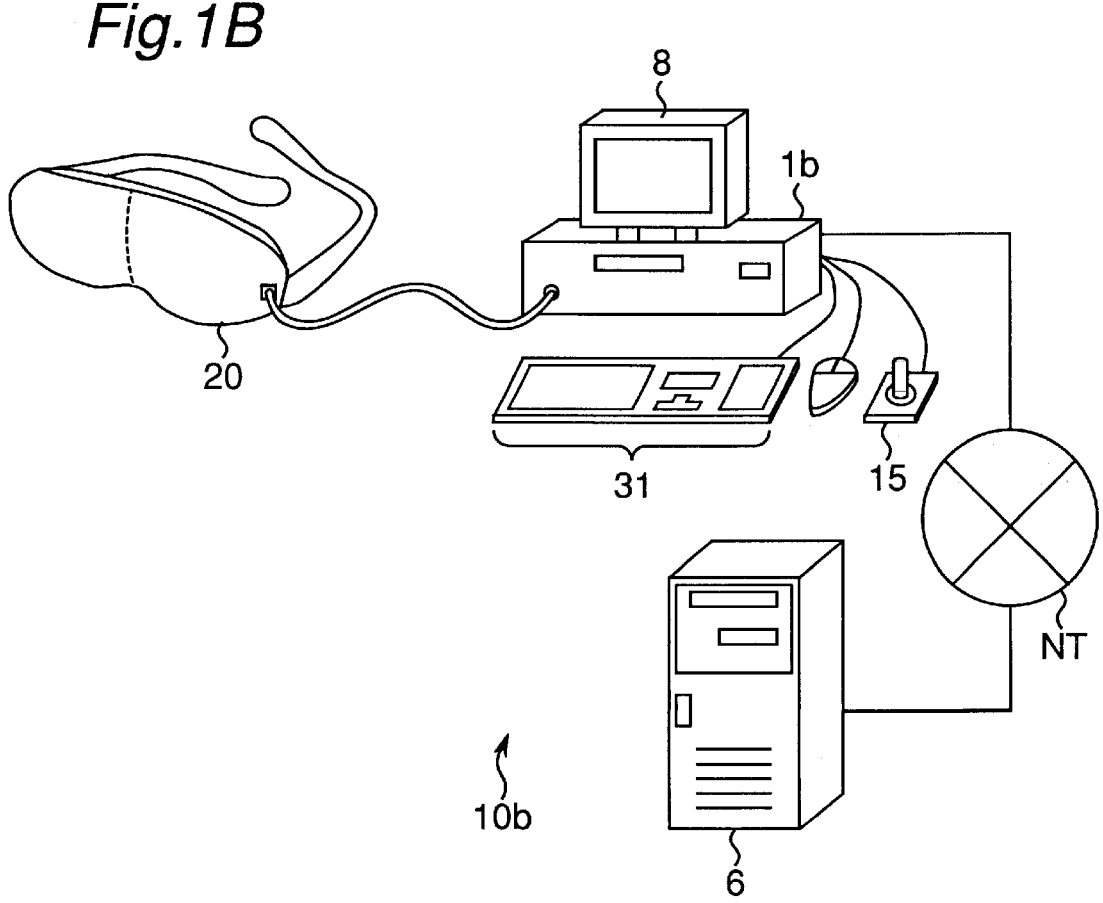
FIG. 1B is a diagram of the appearance of a brain function examining system according to the present invention.

FIG. 1B is a diagram of the appearance of brain function examining system 10b. Brain function examining system 10b includes a controller 1b, an imaging unit 20 of the pupil shown as goggles, and a database server 6. Imaging unit 20 and database server 6 are connected via network NT such as Internet, etc. The difference in configuration from the brain function examining apparatus shown in FIG. 1A is that the database installed inside controller 1a (FIG. 1A) is installed separately as database server 6 and accumulates each index of the subject via network NT. The advantages of this configuration include the following.

For example, in the case of progressive diseases such as Alzheimer's disease in which the patient has no recognition of his/her disease but the condition gradually progresses from healthy normal to infirmity, it is assumed extremely important to periodically carry out pupillary measurement. As described above, since pupillary changes reflect nervous activity of autonomic nervous system and eye movements reflect higher activity of the brain, they are important examination items in examining neuropathy.

However, under the present circumstances, it is not popular to carry out periodical examination of pupillary changes and/or eye movements. In general, people visit doctors because they feel something abnormal in their mind or body and few people periodically go to hospital while they are healthy and normal, and the people are apt to neglect to undergo periodical examinations. Furthermore, even if the measurement is carried out individually, it is extremely difficult for each person to construe the results.

Consequently, it is too late when the doctor diagnoses and a problem of inability to take effective prescription results.

This contrasts with blood pressure, body temperature or other examination indexes which deeply permeate into the society and allow general individuals to possess measuring instruments and to carry out health care by themselves.

Therefore, brain function examination system 10b that can achieve brain examinations based on the measurement of pupillary changes and/or eye movements at home becomes effective by carrying out the measurement of pupillary changes and/or eye movements for brain examination at home of the subject or at public facilities and transmitting the results to the database server via network NT. Database server 6 accumulates the measurement results received and transmits the measurement results of other subjects which have been already accumulated. Based on the transmitted data of other subjects, the brain functions of the subject for which the pupillary changes and/or eye movements are measured can be determined. In such event, if database server 6 carries out multivariate analysis to be described in Embodiment 2 and transmits the results, brain functions can be determined much more easily.

The technique for transmitting and receiving subjects' data via network NT and determining brain functions has been described in detail in the specification and drawings of Japanese Patent Application No. 2000-293076 applied by the same assignee of the present application, and the contents are incorporated in the present specification for reference.

Referring now to the accompanying drawings, preferred embodiments of the present invention will be described. The "brain function examining apparatus" referred to in embodiments has the configuration recited in FIG. 1A, and the controller is a general-purpose PC. However, the "brain function examining apparatus" should include the system of the configuration recited in FIG. 1B.

(Embodiment 1)

Figure 2:
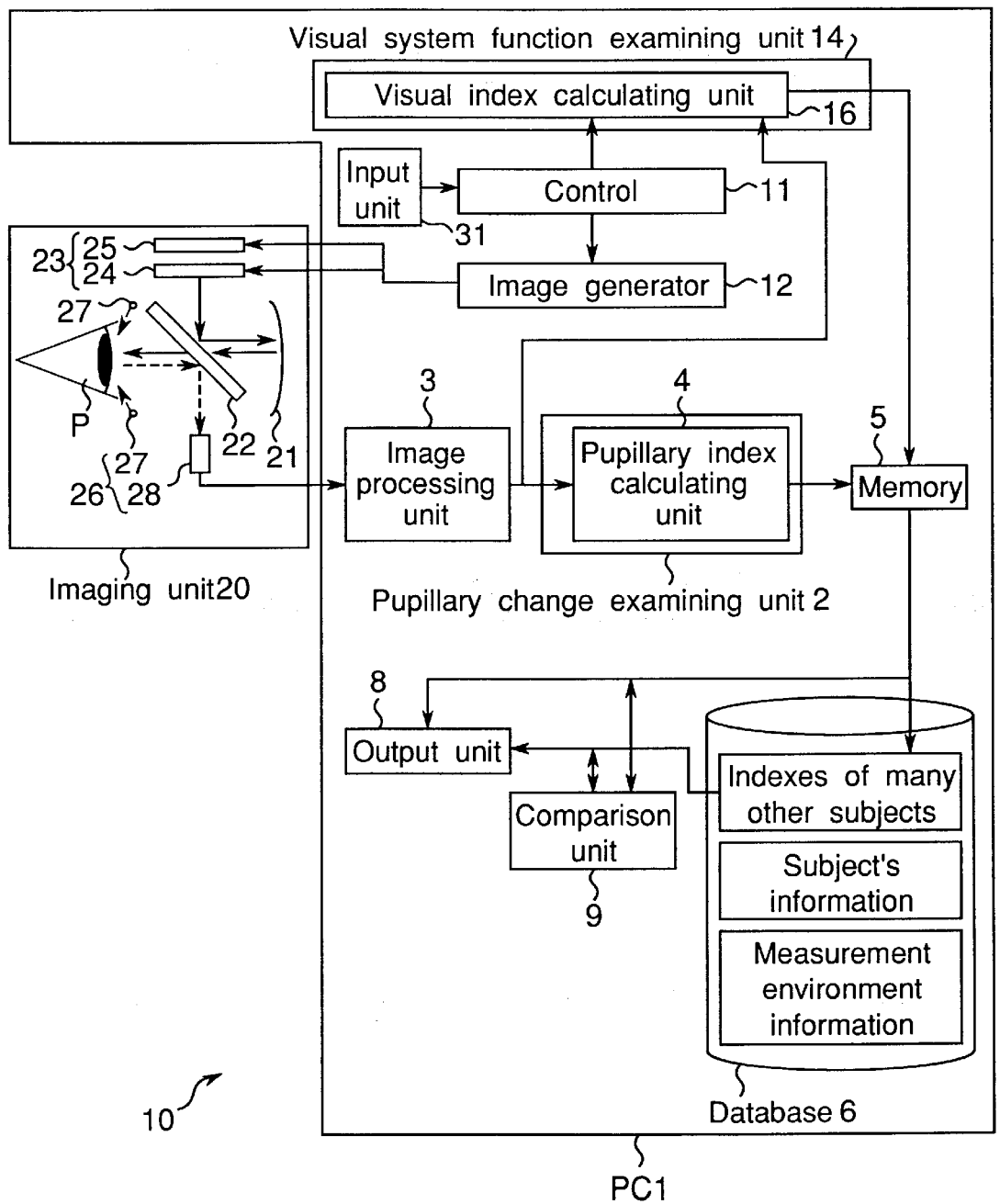
FIG. 2 is a block diagram of the configuration of a brain function examining apparatus according to Embodiment 1.

FIG. 2 is a block diagram showing the configuration of brain function examining apparatus 10 according to Embodiment 1. Brain function examining apparatus 10 is described to find the pupillary index and the visual index of plural types of indexes. As already discussed, brain function examining apparatus 10 includes PC1 and imaging unit 20.

First of all, the detailed configuration of imaging unit 20 will be described as follows.

Imaging unit 20 calculates the pupillary index by irradiating the subject pupil with light to vary the pupillary size and detecting the variations. Imaging unit 20 also calculates the visual index induced by eye movements which is easily obtained by detecting the center of the pupil in images. Imaging unit 20 comprises a concave mirror 21 located in front of the eyes of the subject, a translucent mirror 22 located between subject's eyeball P and concave mirror 21, an image display unit 23 located above translucent mirror 22, and an eyeball imaging unit 26. Translucent mirror 22 is also known as a beam splitter or a beam combiner. In Embodiment 1, concave mirror 21, translucent mirror 22, image display unit 23, and eyeball imaging unit 26 are provided in two sets each for both eyes.

Image display unit 23 comprises an LCD panel 24 and a backlight 25 for irradiating LCD panel 24 with visible light from the back surface side, and is controlled by image generator 12 later described. Image display unit 23 projects the image and reflects it against translucent mirror 22, and presents the virtual image formed by concave mirror 21 to the subject through translucent mirror 22.

Figure 3:
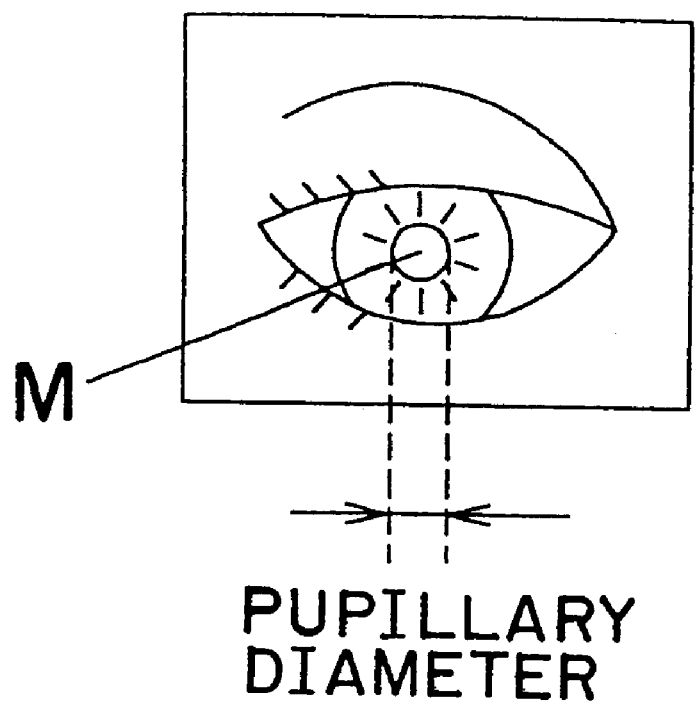
FIG. 3 is a diagram of the pupil imaged by the eyeball imaging unit.

Eyeball imaging unit 26 is disposed for imaging the pupil. Eyeball imaging unit 26 includes a light-emitting diode that emits infrared ray light of infrared ray wavelength (hereinafter called the "infrared ray light LED") 27 and Charge Coupled Device (herein referred to as "CCD") camera 28 for imaging eyeball P of the subject. Infrared ray light LED 27 is arranged in the vicinity of subject's eyeball P in such a manner as to prevent it from disturbing the subject visual field, and irradiates subject eyeball P with the infrared ray light. Since the subject never senses the light from infrared light ray LED 27, it is possible to alleviate uneasiness of the subject. On the other hand, the CCD camera 28 is disposed below translucent mirror 22, that is, on the side opposite to image display unit 23 with translucent mirror 22 in-between, and acquires the image of subject's eyeball P. CCD camera 28 is equipped with an infrared ray transmitting type filter, and is sensitive to infrared rays. Consequently, even under the dark environment with little light quantity of natural light, the CCD camera can image subject eyeball P by the infrared ray light reflected at translucent mirror 22. It is noted that, in place of CCD camera 28, the MOS type imaging element, so-called CMOS sensor or other imaging elements may be used. FIG. 3 is a diagram of pupil M imaged by eyeball imaging unit 26.

Referring to FIG. 2 again, concave mirror 21 does not transmit but reflects the incident light. It is allowed to provide concave mirror 21 with the properties to reflect part of the incident light and to transmit the remainder. Designing the eyeball imaging unit in such a manner to allow the subject to see the outside situation through the concave mirror could alleviate uneasiness of the subject under examination.

Translucent mirror 22 has the wavelength selective layer for reflecting infrared ray light coated on the surface on the CCD camera side and the semi-transmitting layer that reflects part of the visible light and transmits the remainder coated on the surface on image display unit 23 side. Providing the wavelength selectivity to translucent mirror 22 in this way enables efficient utilization of infrared rays. That is, because in Embodiment 1, the infrared rays irradiated from infrared ray light LED27 is used for the environmental light to image the pupil, it is preferable to allow as much infrared rays as possible to impinge on CCD camera 28. Consequently, by providing surface treatment to reflect infrared rays against the surface of translucent mirror 22 as much as possible, the pupil can be imaged by CCD camera 28 without losing the light quantity of infrared rays.

Next description will be made on the configuration and action of PC1. PC1 comprises a pupil change examining unit 2, image processing unit 3, memory 5, database 6, output unit 8, comparison unit 9, control 11, image generator 12, and visual system function examining unit 14.

The test personnel who carries out the brain function examination of the subject chooses whether to measure the pupillary index that reflects the activity condition of the autonomic nervous system, or to examine the visual system functions that reflect the activity condition of the visual cortex of the brain. According to the choice results, the control 11 allows image generator 12 to generate the desired image data and image display unit 23 to display the generated image.

First of all, description is made on the case in which the pupillary index related to light reflex is measured. Image generator 12 turns on the backlight for the specified time from the condition in which backlight 25 is turned off, and displays the completely white image for the desired time. In Embodiment, for optical stimuli for inducing pupillary changes, a flashlight is used. The flashlight is the light which turns on light irradiation only for a short time under the condition free of optical stimuli and immediately stops optical stimuli. Note that it is possible to consider the case in which the optical stimuli are stopped only for a short time under the condition with optical stimuli. However, the optical stimuli of the former are effective for confirming accurate pupillary changes.

Image processing unit 3 detects changes of the pupillary diameter and calculates the pupillary index. By measuring the pupillary light reflex, characteristics of pupil can be known. The pupillary characteristics falls into two broad general categories: static characteristics and dynamic characteristics of the pupil. Image processing unit 3 extracts the pupillary section from the pupillary image (FIG. 2) imaged by CCD camera 28 and finds the size of pupil M and the center point of the pupil. The center point of the pupil is used to calculate eye movement The extraction of the pupillary section is achieved by extracting the pupillary section by the electronic circuit by the use of Video signals (NTSC signals) and acquiring the information concerning the profile of pupil M, for example, information that shows the end-point position which forms the edge of the pupil. For the size of pupil M, the pupillary area or pupillary diameter is considered. In Embodiment 1, the pupillary diameter is found as the size of pupil M.

The pupillary change examining unit 2 primarily includes a pupillary index calculating unit 4. Pupillary index calculating unit 4 calculates the pupillary index based on the changes of the pupillary diameter obtained by image processing unit 3. The pupillary index can be classified into indexes concerning various static characteristics or dynamic characteristics later discussed.

Figure 4:
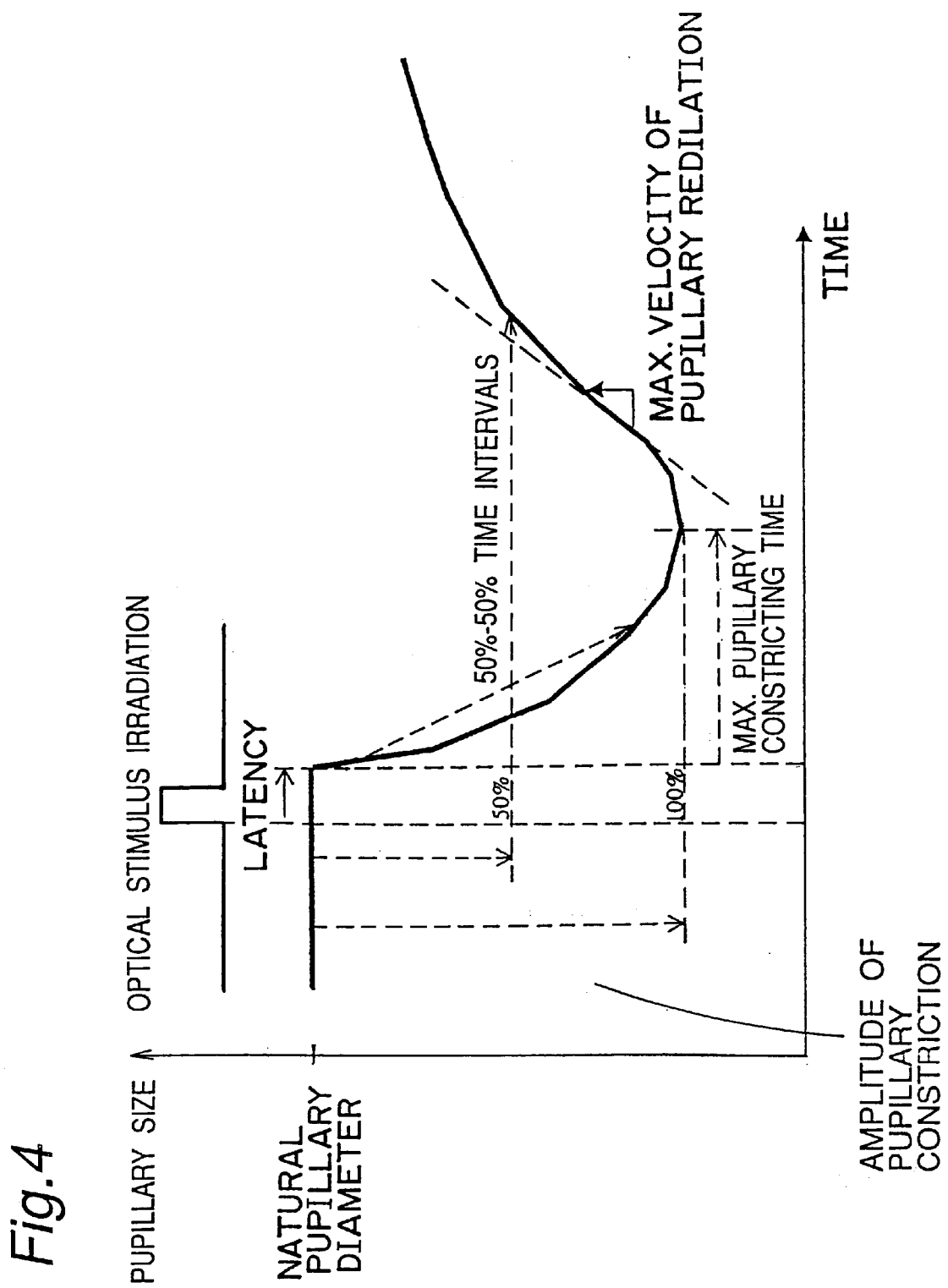
FIG. 4 is a diagram of changes with time of pupil diameter of the subject when optical stimulus is given by the stepped light using the image display section.

Now, discussion will be made on the index concerning the static characteristics or dynamic characteristics of the pupil which are deduced by pupillary index calculating unit 4. FIG. 4 shows changes of subject's pupillary diameter with time when optical stimuli are given by the step light using image display unit 23 (FIG. 1). The pupil reaction to short-time flashlight generally takes place in such a manner that the pupil constricts (called myosis (pupillary constriction)) which occurs with a slight time lag from the start of optical stimuli and redilates (called mydriasis (pupillary redilation)) after the pupil becomes the smallest. For these pupillary changes, various indexes can be defined as shown in FIG. 4. Specifically, initial pupillary diameter, latency of the response, pupillary constriction time, pupillary redilation time, amplitude of pupillary constriction, pupillary constriction ratio, pupillary constriction velocity, pupillary redilation velocity, pupillary constriction acceleration, maximum pupillary constriction velocity, maximum pupillary redilation velocity, maximum pupillary acceleration time, etc. are considered. Of these, the initial pupillary diameter is the index concerning the static characteristics which are not caused by optical stimuli. On the other hand, the elements other than the initial pupillary diameter is the index concerning dynamic characteristics induced by optical stimuli. It is noted that the irradiation time of optical stimuli in FIG. 3 is about 0.1 seconds by flashlight, but the lighting time of the flashlight may be shorter or longer than 0.1 seconds and is not subject to any particular restriction.

The initial pupillary diameter is the size of pupil M at the normal time before optical stimuli are given. For other definitions, it may be the size of pupil M at an optional time before optical stimuli are given or may be the time average of the size of pupil M at optional time intervals before optical stimuli are given. Furthermore, even after the optical stimuli are given, it may be the size of pupil M at the optional time before pupillary constriction begins or may be time average of the size of pupil M at optional time intervals.

The latency refers to a length of time required for the pupil to respond to the light stimulus subsequent to application of the light stimulus to the pupil. As is well known to those skilled in the art, the pupil does not necessary respond to a light stimulus the exact moment the light stimulus is applied, and has a delay in response. Specifically, this delay is a cumulation of the length of time required for the light stimulus to be photoelectrically converted into electric impulses that are subsequently transmitted to the ophthalmic nerve; the length of time required for secretion of a chemical substance, known as a neurotransmitter, that transmits the nerve impulses across intercellular gaps; the length of time required for the effector to drive the smooth muscle in response to the electric impulses appearing at the centrifugal nerve ending; and so on.

There is about 0.2 seconds to 0.3 seconds for latency, and in the case of the flashlight shorter than this, it is possible to set measurement conditions in which no optical stimuli exist during pupillary changes.

The pupil constricted time refers to the length of time as measured between certain timings during constriction of the pupil taking place in response to the light stimulus. Specifically, the length of time during the pupillary constriction takes place from start to end is referred to as the maximum pupil constricted time. While the difference between the natural pupillary diameter and the pupillary diameter measured at the end of the pupillary constriction is referred to as a total amount of the pupil constricted or an amplitude of pupillary constriction, the length of time required for the pupillary diameter to decrease 50% relative to that measured at the start of the papillary constriction is referred to as the 50% pupil constricted time. By the same token, 10% and 90% pupil constricted times represent the lengths of time requires for the pupillary diameter to decreases 10% and 90%, respectively, relative to that measured at the start of the pupillary constriction. 10–90% pupil constricted time represents the time span between the timing of 10% constriction of the pupillary diameter and the timing of 90% of the pupillary constriction. Thus, the pupil constricted time used herein is a general term used to encompass various times associated with the pupillary constriction.

The pupillary constriction ratio stands for the ratio of the amplitude of pupillary constriction the amplitude of pupillary constriction divided by the natural pupillary diameter.

The velocity of pupillary constriction, or the pupillary constriction velocity, refers to the amount of change of the amplitude of pupillary constriction per unitary time and can be defined in numerous ways depending on how the unitary time is reckoned. The maximum velocity of the pupillary constriction refers to the maximum value of velocity occurring during change of the pupillary diameter upon constriction with passage of time.

The acceleration of pupillary constriction refers to the rate of change of the pupillary constriction velocity per unitary time and can, as is the case with the pupillary constriction velocity, be defined in numerous ways depending on how the unitary time is reckoned. The maximum acceleration of the pupillary constriction therefore refers to the maximum value of acceleration occurring during change of the pupillary diameter upon constriction with passage of time. The length of time necessary to attain the maximum velocity of pupillary constriction refers to the length of time required to attain the maximum velocity of pupillary constriction subsequent to start of the pupillary constriction.

The velocity of pupillary radiation, or the pupillary radiating velocity, refers to the amount of radiation of the pupil, or the pupil redialed amount, per unitary time and can be defined in numerous ways depending on how the unitary time is reckoned. The maximum velocity of pupillary radiation refers to the maximum value of velocity occurring during change of the pupillary diameter upon redilation with passage of time. The length of time necessary to attain the maximum velocity of pupillary redilation refers to the length of time required to attain the maximum velocity of pupillary redilation subsequent to start of the pupillary constriction or redilation whichever chosen as desired. In the illustrated embodiment, the former definition is employed.

50%–50% time interval refers to the length of time that passes from the timing at which the pupil has constricted 50% of the amplitude of pupillary constriction to the timing at which the pupil being redilated returns to the 50% pupil constricted amount. This 50%–50% time interval is an index comprises of a combination of respective indexes indicative of the pupil constricting time, or the time during which pupillary constriction takes place, and the pupil redilating time or the time during which pupillary redilation takes place, respectively.

In the definitions of the indexes, optical stimuli are considered as flashlight but the step light may also be considered optical stimulus conditions, which continuously holds the lighted condition with a constant light quantity after the light is turned on. In the case of the step light, indexes concerning pupillary changes shown in FIG. 3 can be defined as is the case of the flashlight. However, in such event, it is likely to become difficult to find the point in which pupil M becomes the minimum as the light quantity increases.

Next discussion will be made on the case in which the visual system functions are examined. Based on the instructions from control 11 (FIG. 2), image generating unit 12 (FIG. 2) presents an image for examination to the subject. FIG. 5 shows the example of the image for examination. The image for examination is, for example, the image in which five circles are arranged on the black background screen. One of the five circles is located at the screen center and the remaining four circles are located as if they surround the center circle and remaining four circles are arranged in top and bottom and right and left positions with respect to the center circle, respectively. Of the four circles surrounding the center circle, the color same as that of the center circle is used for optional three circles (shown in solid slanting lines) and the color of the remaining one circle is different from that of the center color but very similar to it (shown in dotted slanting lines). For example, the color of the circles located at the top, at the bottom, and on the right to the center circle is blue and the color of the circle located on the left to the center circle is blue but paler than that of the center circle.

Referring now to FIG. 2 again, the visual system function examining unit 14 includes a visual index calculating unit 16 and an input unit 15 such as a joystick (not shown). The test personnel presents a task to the subject, "Choose one out of four circles located in the surrounding whose color is different from the color of the circle located at the screen center, and flip the joystick to the direction where the circle you chose is located." When the subject selects any of the circles for this task and enters the circle chosen by the use of input unit 15 (FIGS. 1A and 1B), visual index calculating unit 16 deduces the visual index based on the contents of the visual system function examination entered from control 11 and, optionally, the information entered by the subject using input unit 15.

In the above example by use of input unit 15, the visual indexes thus obtained may include characteristics of not only brain functions but motion functions of the subject. Therefore, in order to calculate accurate visual indexes which only reflects brain functions, it is preferable to calculate visual indexes without motional input unit 15 such as a joystick. Thus, preferable calculation scheme of visual indexes is described as follows.

FIG. 18 is a diagram of an example of the image for examination. Initially, a target image (×) is displayed in the center of display area of concave mirror 21 of FIG. 2. The test personnel presents a task to the subject, "Look at the target for a period. As the target disappears and again appears at one of the four corners of the display area, find and look at the target as soon as possible." In such an example, a response time from re-appearance of the target to actual completion of the eye movement can be used for an evaluation index so as to achieve quantitative evaluation of perceptive function. This means that a third party can readily judge whether the subject looks at the target or not objectively. Further, by recording the eye movements, judgement can be automated. Note that the response time is available as an input variable of multivariate analysis calculation described later.

Reference 1 mentioned above reports that there is a statistically significant difference in color identification capacity (p=0.05) between the subject group suffering from Alzheimer's disease and the healthy normal group, and in particular, in the subject group suffering from Alzheimer-type dementia, the color identification capacity particular to blue degrades. In Embodiment 1, the visual index is deduced by carrying out the visual test as described above.

Memory 5 is a storage unit of PC1, and is, for example, random access memory (RAM). Memory 5 stores the pupillary index and visual index obtained at pupillary index calculating unit 4 and visual index calculating unit 16.

Database 6 is constructed by the use of the secondary memory unit such as a hard-disk drive, etc. of PC1, and accumulates indexes prescribed with individual pupillary index and visual index set as the criteria of one or more subjects, whose indexes have already been deduced (hereinafter called the "reference pupillary index," and "reference visual index," respectively). In addition to these indexes, subject's information necessary for brain function examination such as age of each subject, sex, anamnesis, present disease, measurement date and time, measuring place, environmental conditions such as illuminance, temperature, etc., results of intelligence test, etc., measurement environment information, etc. are stored. Consequently, the reference pupillary index and the reference visual index can be extracted in accord with the age, sex, name of disease (Alzheimer's disease, dementia, Meniere disease, vertigo), etc. In Embodiment 1, it is configured to add the index data of the relevant subject stored in memory 5 as well as subject information of the relevant subject, measurement environment information, etc. to database 6 as new data. Accordingly, every time the brain function examination is carried out, the examination results are accumulated as new data and since the data of increasing number of subjects are accumulated, database 6 with high reliability can be constructed.

Output unit 8 is a display unit such as a display device or a printer. To output unit 8, indexes of the relevant subject and other subjects are outputted and displayed. Specifically, output unit 8 displays the pupillary index and the visual index of the relevant subject obtained from the pupillary index calculating unit 4 and the visual index calculating unit 16 together with the pupillary indexes and the visual indexes of a large number of subjects accumulated in database 6. Consequently, the test personnel, etc. can compare each of the indexes of the relevant subject with the indexes of other subjects accumulated in database 6 and can easily judge what kind of values the indexes of the relevant subject relatively indicate. The indexes indicated may be not only individual indexes of other subjects but also averages of a plurality of subjects or averages of some specific subject groups. In addition, the indexes of the relevant subject obtained in the past may be utilized. By comparing with the past symptoms, the progressive disease can be easily found and the degree of progress can be easily determined.

Needless to say, not only single index but also two or more indexes may be outputted and displayed simultaneously. Thus, the test personnel, etc. can grasp more reliably how far or how close the measurement results of the relevant subject are to the healthy normal people or patients suffering from encephalopathy. It is noted that when it is possible to determine with the relative measurement results alone of the subject, indexes of other subjects accumulated in database 6 may not be displayed.

Comparison unit 9 compares the pupillary index calculated at pupillary index calculating unit 4 and/or visual index calculated at visual index calculating unit 16 with the corresponding reference indexes accumulated in database 6. Comparison unit 9 can output the comparison results to output unit 8. Furthermore, it can also output the information on how much difference exists, etc. Comparison unit 9 is constructed by the use of the calculating capacity of PC1. In the form of the brain function examination system 10*b* (FIG. 1B), the comparison unit may be installed at database server 6 (FIG. 1B). The comparison unit acquires the subject indexes via network NT. The comparison results are transmitted to controller 1*b* (FIG. 1B) via network NT.

It is possible to provide the comparison unit with a capacity to determine the brain function condition of the subject. In such event, comparison section 9 prepares the judgment criteria for determining the brain functions. For example, a certain threshold value is provided and if the difference between the subject pupillary index and the reference pupillary index of dementia patients is greater than the threshold value, the subject is highly liable to suffer from dementia. Providing a plurality of threshold values enables further subtle comparison and determination as to how closer to dementia the case would be.

Pupillary index calculating unit 4, control 11, image generator 12, and visual index calculating unit 16 can be achieved by the arithmetic processing capacities of PC1 represented by the central processing unit (CPU).

The various component parts of the brain function examining apparatus 10 have been described above. In the next place, the operation of brain function examining apparatus 10 of the structure hereinabove described will be described. It is to be noted that although various operation of brain function examining apparatus 10 are performed by the various component parts there of described above, the sequence and overall control of operation of brain function examining apparatus 10 are carried out by a control unit 11 (FIG. 2)

Figure 6:
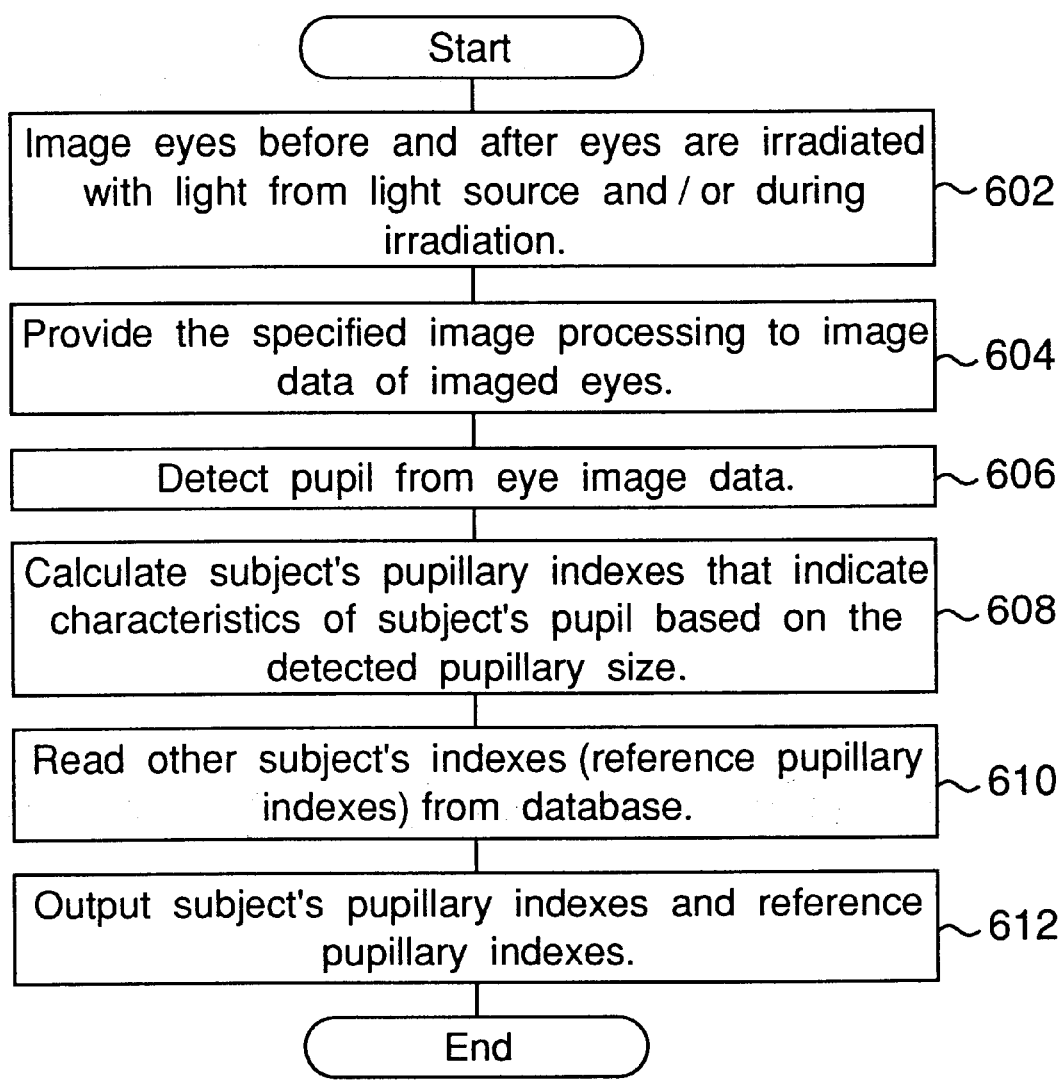
FIG. 6 is a flow chart of the operation sequence of the brain function examining apparatus concerning the pupillary index.

FIG. 6 illustrates the flowchart showing the sequence of operation of the brain function examining apparatus 10. With brain function examining apparatus 10 electrically powered on, CCD camera 28 of imaging unit 20 monitors subject's eye P (FIG. 2) before, after and/or during illumination with light emitted from light source 27 (FIG. 2) (step 602). Image data indicative of subject's eye P (FIG. 2) imaged by CCD camera 28 are outputted from CCD camera 28 to image processing unit 3 (FIG. 2). Image processing unit 3 (FIG. 2) in response to receipt of the image data from CCD camera 28 performs a predetermined image processing (step 604). Image processing unit 3 detects the pupil from the image data which is performed a predetermined image processing (step 606). When the pupil is detected, the pupillary diameter is determined. Based on the pupillary diameter so determined, index calculator 4 (FIG. 2) calculates the subject indexed indicative of the characteristic of the subject's pupil (step 608). On the other hand, the central processing unit (not shown) of brain function examining apparatus 10 reads out from database 6 (FIG. 2) the index of the other subject what can be used as the base index described above (step 610). This central processing unit (not shown) outputs the calculated subject index and the base index to output unit 8 (FIG. 2) (Step 612). For example, when latency is outputted, the reference index numerical values are displayed by a graph and at the same time, the latency of the subject is displayed by an auxiliary line as "your latency" overlapping over the graph.

Figure 7:
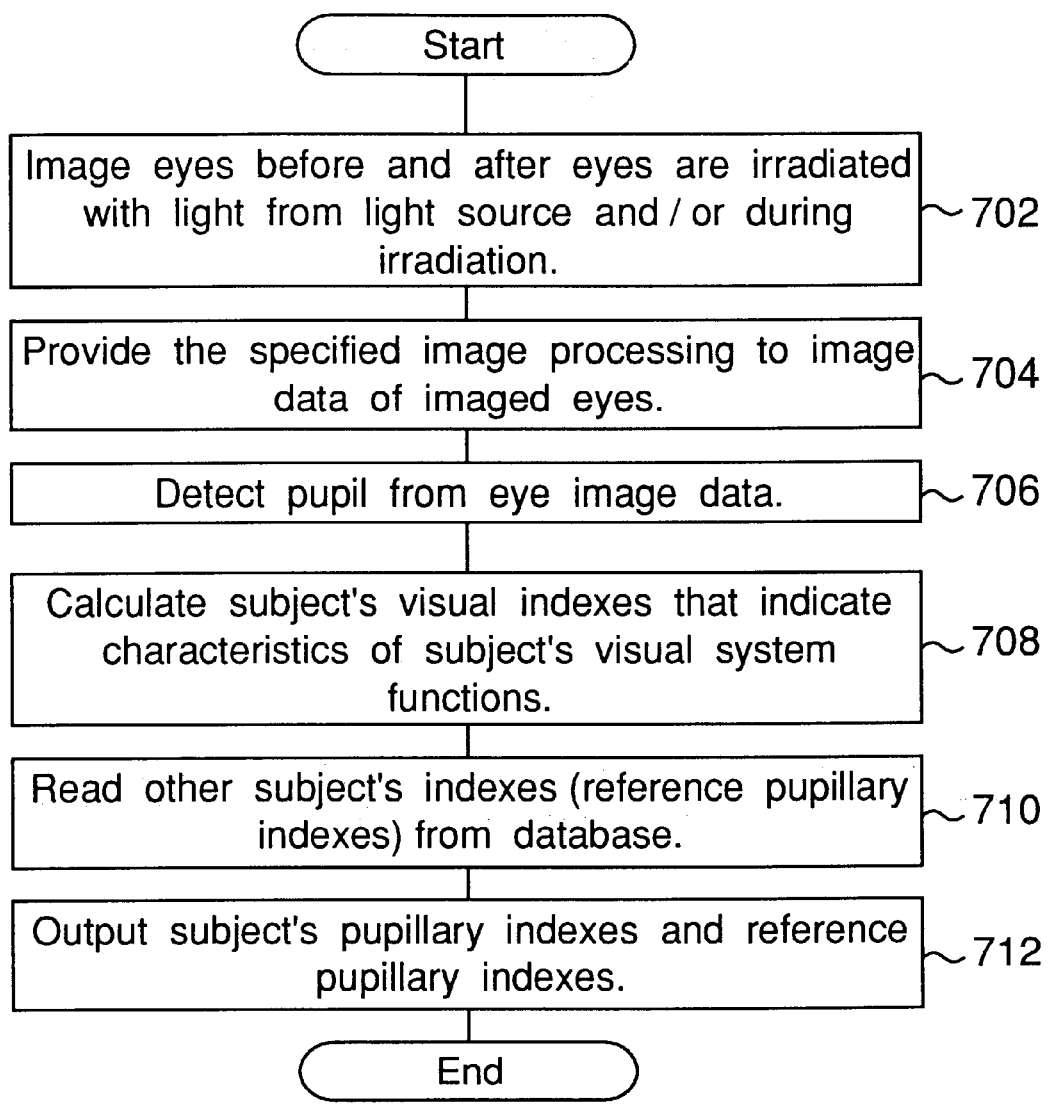
FIG. 7 is a flow chart of the operation sequence of the brain function examining apparatus concerning the pupillary index.

Next discussion is made on the operation concerning the visual index of the brain function examining apparatus 10. FIG. 7 is a flow chart showing the operation procedure concerning pupillary index of brain function examining apparatus 10. First of all, brain function examining apparatus 10 (FIG. 2) displays the examination image (for example, FIG. 5) on image display unit 23, then CCD camera 28 of imaging unit 20 (FIG. 2) monitors subject's eye P before, after and/or during illumination with light emitted from light source 27 (FIG. 2)(Step 702). In response to receipt of the image data from CCD camera 28, image processing unit 3 (FIG. 2) performs a predetermined image processing (Step 704). When image processing unit 3 detects the pupil from the image data which is performed a predetermined image processing (Step 706), the system calculates the subject visual index that indicates the characteristics of the visual system functions of the subject (Step 708). The system reads out from database 6 the indexes of other subjects (reference visual indexes mentioned above) (Step 710). The central processing unit (not shown) outputs the calculated subject's visual index and reference visual indexes to output unit 8 (FIG. 2) (Step 712).

As described above, brain function examining apparatus 10 carries out calculations for each of the pupillary indexes and visual indexes. Since the apparatus displays and outputs the subject indexes and reference indexes of other subjects with respect to physiological indexes of different types such as pupillary index and visual index, the doctor and the test personnel can determine the brain functions easily, highly accurately, and highly reliably.

Noted that the pupillary index at the pupillary change examining unit 2 and the visual index at the visual system function examining unit 14 may not be calculated by one PC. For example, two PCs are disposed and pupillary change examining unit 2 and visual system function examining unit 14 may be achieved by each of the PCs, respectively. In such event, two PCs communicate with each other and transmit and receive the calculated indexes.

(Embodiment 2)

In Embodiment 1, the calculated subject's indexes and the reference indexes stored in advance in database 4 are outputted. In Embodiment 2, the multivariate calculation is carried out for converting a large number of indexes used for brain function examination into fewer indexes and using these converted indexes, the brain functions are examined. Now, the brain function examining apparatus according to Embodiment 2 will be described as follows. However, the description on the component elements same as those of the brain function examining apparatus according to Embodiment 1 (FIG. 2) will be omitted and different component elements only are described.

Figure 8:
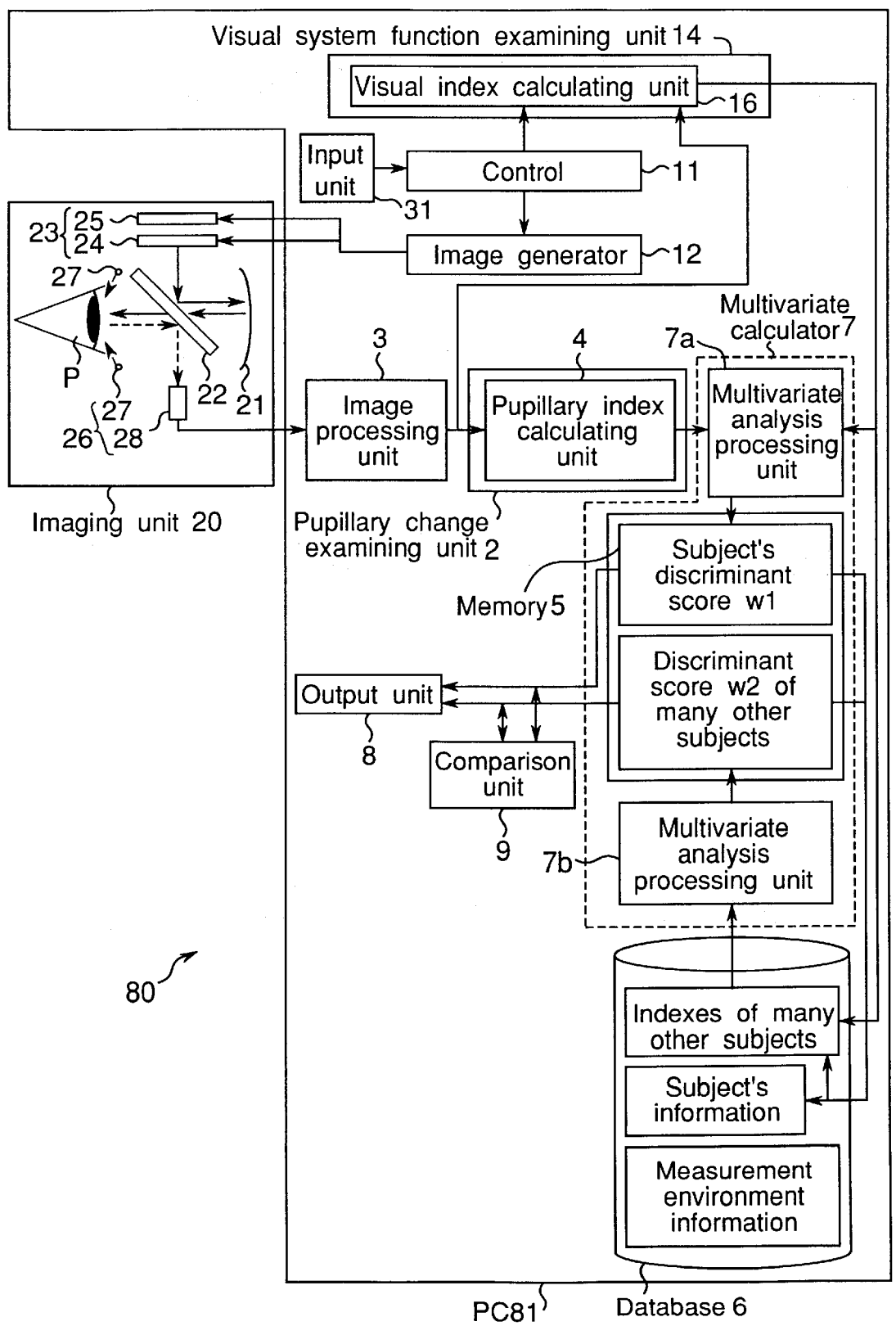
FIG. 8 is a block diagram of the configuration of a brain function examining apparatus according to Embodiment 2.

FIG. 8 is a block diagram showing the configuration of the brain function examining apparatus according to Embodiment 2. What the brain function examining apparatus 80 differs from the brain function examining apparatus 10 (FIG. 2) is the installation of the multivariate calculator 7. The memory 5 is assumed to be included in the multivariate calculator 7 for convenience of description.

As described in Embodiment 1, there exist generally a plurality of pupillary indexes deduced by the pupillary index calculating unit, and it is quite troublesome to confirm each of all the indexes. Consequently, if it is possible to reduce the number of indexes as much as possible, the operation for confirming the indexes can be simplified. Therefore, in the brain function examining apparatus 80 according to Embodiment 2, multivariate calculator 7 is installed to carry out multivariate analysis calculation for converting a plurality of indexes calculated by pupillary index calculating unit 4 and visual index calculating unit 16 into fewer indexes. Thus, it is possible to examine brain functions using fewer converted indexes.

Now, multivariate calculator 7 will be described more in detail. Multivariate calculator 7 chooses the discriminant score by various pupillary indexes and visual indexes by the discrimination analysis method in multivariate analysis. This discriminant score is generally one in many cases but a plurality of discriminant scores may be found from all the pupillary indexes and visual indexes as a result by classifying pupillary indexes and visual indexes into several groups and finding one discriminant score for each group. In Embodiment 2, description will be made with the discriminant score set to one.

The discrimination analysis by multivariate analysis is a technique to put together the information on a plurality of indexes, convert them into one discriminant score, and carry out some kind of analysis judgment) using the discriminant score. For other multivariate analysis technique, there is a principal component analysis technique. This is a technique to convert a plurality of indexes into fewer indexes and to put together a large number of original indexes into fewer pieces of information. It can be said that it is a technique for generalizing the pretreatment other than judgment of the previous discrimination analysis technique. Converting into fewer indexes can reduce the number of targets to be handled and can achieve quick processing.

Multivariate calculator 7 is achieved by the use of the calculating functions of PC 81. However, it may be achieved by using separate apparatus. For example, it may be achieved by the use of DSP (digital signal processor) or microcomputer without using the personal computer. Furthermore, as described referring to FIG. 1B, when database 6 is constructed by installing a database server, multivariate calculator 7 can be achieved by the use of the calculating functions of the database server.

Now, for Embodiment 2, the method for deducing the discriminant score based on the discrimination analysis method is described as follows. The multivariate analysis technique is not particularly limited to the embodiment. Needless to say, the first principal component or a plurality of principal components in the principal component analysis technique may be employed as representative values in place of the discriminant score in Embodiment 2. For the multivariate analysis technique, reference may be made to "Igaku Tokeigaku Handobukku (Handbook of Medical Statistics)," edited by Hideo Miyahara and Toshiro Tango and published in 1995 by Asakura Publishing Co., Ltd.; "Tahenryo Deta Kaiseki Nyumon (Introduction to Multivalue Data Analysis)" by Takaichi Sugiyama published in 1983 by Asakura Publishing Co., Ltd.; "Hisenkei Tahenryo Kaiseki—Nyurarunetto-niyoru Apurochi (Nonlinear Multivariate Analysis—Approach by Neural Network) published in 1996 by Asakura Publishing Co., Ltd., etc.

Multivariate calculator 7 includes a multivariate analysis processing unit 7a and 7b and memory 5. Memory 5 is the same as described in Embodiment 1. Multivariate analysis processing unit 7a converts a plurality of indexes concerning static or dynamic characteristics of the subject's pupil obtained at pupillary index calculating unit 4 and the visual indexes found at visual index calculating unit 16 into fewer indexes and calculates the discriminant score w1 of the relevant subject. Multivariate analysis processing unit 7b calls out the pupillary indexes and visual indexes of a large number of subjects stored at pupillary index calculating unit 4 and visual index calculating unit 16 and then stored in database 6, carries out multivariate analysis calculation, and calculates the discriminant score w2 of a large number of subjects.

In database 6, discriminant scores w1 and w2 are further stored. Since the discriminant score of the examination results is accumulated in database 6 as a new data every time the brain function examination is carried out, the data of still more subjects are accumulated and highly reliable database 6 can be constructed.

Comparison unit 9 compares discriminant scores w1 and w2. In such event, it is possible to output the information as to how much difference exists, etc. When comparison unit 9 judges the condition of subject's brain functions, comparison unit 9 prepares the judgment criteria in advance and performs judgment in compliance with the judgment criteria as is the case of Embodiment 1.

Output unit 8 can display discriminant score w1 of the relevant subject and discriminant score w2 of other subjects simultaneously. For the display mode, same as described in Embodiment, discriminant score w1 of the relevant subject may be displayed overlapping over discriminant value w2 of other subjects. Thus, it is possible to easily determine what kind of value discriminant score w1 of the relevant subject indicates relatively as compared to the discriminant score s2 of other subjects. Noted that the discriminant score of other subjects may not be one discriminant score but the average of the discriminant scores of a plurality of subjects, or may be the average of discriminant scores of a specific subject group. The discriminant scores of the relevant subject obtained in the past may be utilized. By comparing with the past symptoms, it is possible to find a progressive disease and determine the degree of progress easily. The output unit 8 may display pupillary indexes and other data in addition to discriminant scores w1 and w2.

The configuration of the brain function examining apparatus 80 has been described as above. Next discussion will be made on the action of the brain function examining apparatus 80 with the process for finding the discriminant score w1 concerning the pupillary index taken as an example.

Figure 9:
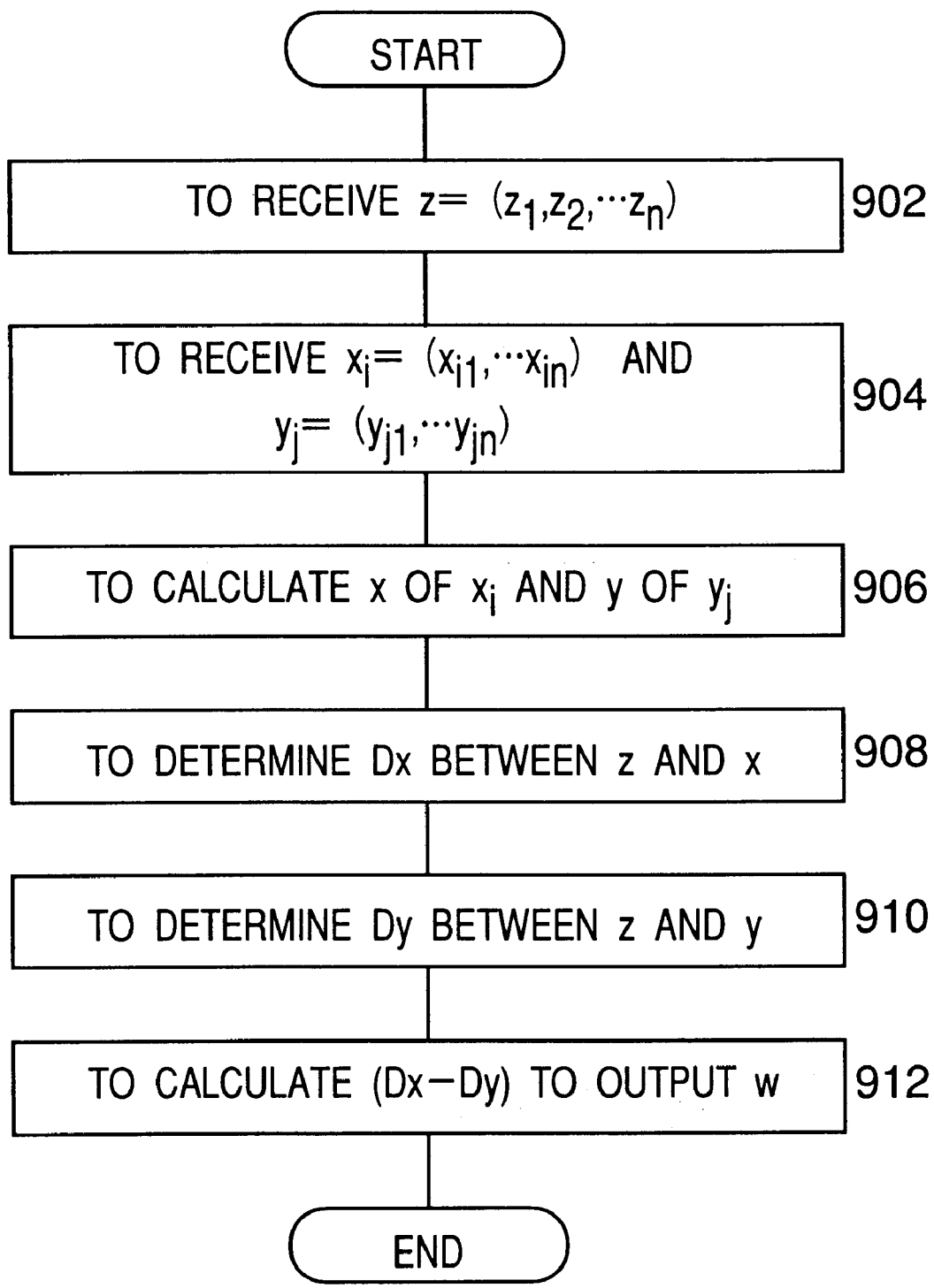
FIG. 9 is a flow chart of the calculation procedure of discriminant score w1 concerning the pupillary index.

FIG. 9 is a flow chart showing the calculation procedure of the discriminant score w1 concerning the pupillary index.

Multivariate analysis processing unit 7a (FIG. 8) first receives a subject index group $z=(z_1, z_2, \ldots, z_n)$ of a certain subject from the index calculator 4 (FIG. 8) at step 902. $z_1$ or the like represents the value of each pupillary index. Multivariate analysis processing unit 7a makes use of, for example, the latency, the natural pupillary diameter, the amplitude of pupillary constriction, the maximum velocity of pupillary redilation, the maximum velocity of pupillary constriction, the time required to attain the maximum velocity of pupillary constriction and the time required to attain the maximum acceleration of pupillary constriction as indexed. Then, multivariate analysis processing unit 7b (FIG. 8) receives a base index group $x_i=(x_{i1}, \ldots, x_{in})$ of a normal subject and a base index group $y_j=(y_{j1}, \ldots, y_{jn})$ of an non-normal subject from database 6 (FIG. 8) at step 904, wherein i and j=1, 2, . . . , and multivariate analysis processing unit 7b receives base index groups of the plural normal and non-normal persons. These $x_{j1}$ and $y_{j1}$ or the like are a value of each index of the normal person i and the non-normal person j and are the same index as the index used as the subject index. Then, an average index group x of base index group $x_i$ of the normal persons and an average index group y of base index group $y_j$ of the non-normal persons are calculated (step 906). The average index group x means an average value of the normal persons for each index. After calculation of average index group $x_1$ the Maharanobis square distance Dx between the index group z for the relevant subject and the average index group x for normal persons is determined (step 908).

The Maharanobis squaredistance can be obtained as $Dx=(z-x)A^{-1}(z-x)^T$ by determining the variance and covariance matrices A of base index group $x_j$, wherein $A^{-1}$ stands for an inverse matrix of A and $(z-x)^T$ stands for the transpose of $(z-x)$. Similarly, Maharanobis square distance Dy between subject index group z and the average index group y is determined at step 910. Finally, (Dx-Dy) is calculated to output the discriminant score w at step 912. By this sequence, the discriminant score can be determined based on the subject index group and the base index group.

In the above example, the calculation procedure of discriminant score w1 was described using the pupillary index only. However, one or more discriminant scores can be calculated by using only a plurality of visual indexes. Two or more discriminant scores obtained by using the pupillary index and the visual index respectively are further employed to calculate one or more integrated discriminant scores. Note that the discriminant score is able to be calculated with the pupillary index and the visual index at a time. For example, two or more pupillary indexes (latency, natural pupillary diameter) and one or more visual indexes (for example, index concerning latency of the saccadic eye movement, variance of the fixation) may be combined. In such event, the above-mentioned calculation is carried out with the indexes concerning latency, natural pupillary diameter, and latency of the saccadic eye movement and/or variance of the fixation used as a subject's index group and three reference indexes corresponding to these indexes used as a reference index group.

Now, the action of brain function examining apparatus 80 (FIG. 8) has been described. In the description mentioned above, the pupillary index was used for an example, but for the visual index, the discriminant score can also be calculated in the exactly same procedures. In addition, using the pupillary index and/or visual index, one or more discriminant scores can be found.

In multivariate calculator 7, the discrimination analysis method was used, but the multivariate calculation by the quadratic discrimination method may be carried out for more strict determination. That is, a method for using the neural network, a method for using a fuzzy theory, or a method for using an expert system.

Now description will be made on the method for using the neural network. The neural network possesses a three-layer structure comprising an input unit, intermediate unit, and output unit. In the learning process, one or more values are calculated from a plurality of indexes, a pair of a certain index and a desirable output value based on that index are given to the network, and the network structure is decided. By giving a plurality of indexes to the network obtained in the learning, the output value can be obtained. In the learning process, the combination weight value is adjusted so that the network output is brought closer to the desirable output value. Repeating the presentation of the index eventually allows the desired output to be displayed even when any index is given to the network. In this way, the brain function is determined by the indexes observed from the subject.

Now the method for using the fuzzy theory will be described. For example, to think of the attributes concerning the index, "short latency" or on the contrary, "long latency" can be considered. When the brain functions are examined, it can be said that higher brain functions are displayed in the case of "short latency" and "quick maximum pupillary constricting time" than in the case of "short latency" alone or "quick maximum pupillary constricting time" alone. In this way, there are $(2^{n-1})$ kinds of evaluation sets with respect to n pieces of attributes. In the fuzzy theory, this kind of set is called the fuzzy set. The fuzzy sets are prepared in advance, and at the time of examination, brain functions are determined by the indexes observed from the subject.

The method for using the expert system will be described. The expert system is a system to provide the machine with the medical field theories and experimental knowledge which doctors, etc. possess and to allow the machine to go through accurate judgment and operation procedures. In the brain function examining apparatus, conditions are given to each index, such as "latency is shorter than 0.2 msec," further "latency is longer than 0.25 msec," etc., and the results when such conditions hold for are set as experimental knowledge. At the time of examination, each index observed from the subject is applied to the condition, respectively, and the brain functions are determined. The neural network, fuzzy theory, and expert system are described in detail in the specification and drawings of Japanese Patent Application No. 2000-340996 of the same assignee, whose contents are incorporated in the present specification for reference. As described above, by the method other than the discrimination analysis method, brain functions can be precisely determined.

(Embodiment 3)

In Embodiments 1 and 2, a visual test concerning latency of the saccadic eye movement and/or variance of the fixation for finding out a circle of a color different from the color of the center circle from five circles is carried out and the indexes concerning the visual system functions are found. From Embodiment 3 to Embodiment 7, examples for finding other kinds of indexes concerning the visual system functions will be described.

There is stereoacuity for one of the visual system functions. In Reference 1 mentioned above, it is reported that there is a statistically significant capacity difference in stereoacuity between the subject group of Alzheimer-type dementia cases and the healthy normal group (p=0.05). Therefore, in Embodiment 3, the indexes concerning the visual system functions will be deduced by carrying out the visual examination concerning stereoacuity. For the brain function examining apparatus according to Embodiment 3, both brain function examining apparatus 10 (FIG. 2) and brain function examining apparatus 80 (FIG. 8) can be used. In the following description, brain function examining apparatus 10 (FIG. 2) is used. What differs is the kind of indexes concerning the visual system functions and there is no difference in calculating the pupillary indexes by pupillary index calculating unit 4 (FIG. 2) and displaying the pupillary indexes and visual indexes.

In Embodiment 3, the stereoacuity is examined by the use of binocular stereoscopic vision method. The binocular stereoscopic vision method is a method for presenting two kinds of image with parallax given by the use of pupillary intervals of both eyes of the human being to both right and left eyes to create the depth feeling.

Figure 10:
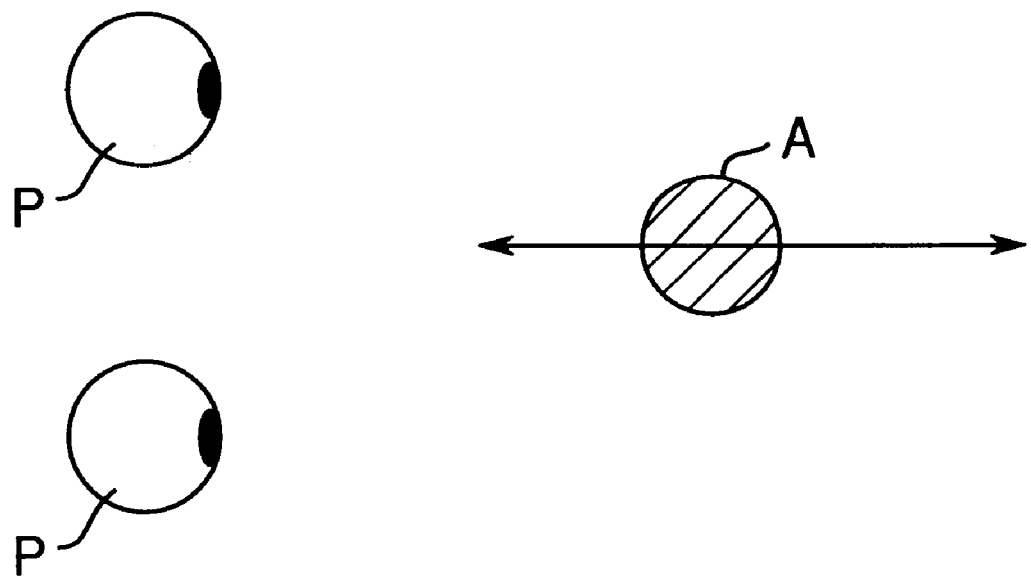
FIG. 10 is a diagram of an example of image for examination.

When the visual system function examination as described above is carried out, image generator 12 (FIG. 2) presents the examination image to the subject using image display unit 23 (FIG. 2). FIG. 10 is a drawing showing an example of the image for examination. For convenience of the description, two eyeballs P are also shown. The images presented to both eyeballs P, respectively, are expressed with the portion corresponding to the parallax of both eyes deviated. Accordingly, fusion A looks like increasing the thickness in the depth direction. The eye movements when the fusion position is continuously moved back and forth in the depth direction are observed from the image of the eyeball imaged by CCD camera 28 (FIG. 2).

Figure 11A:
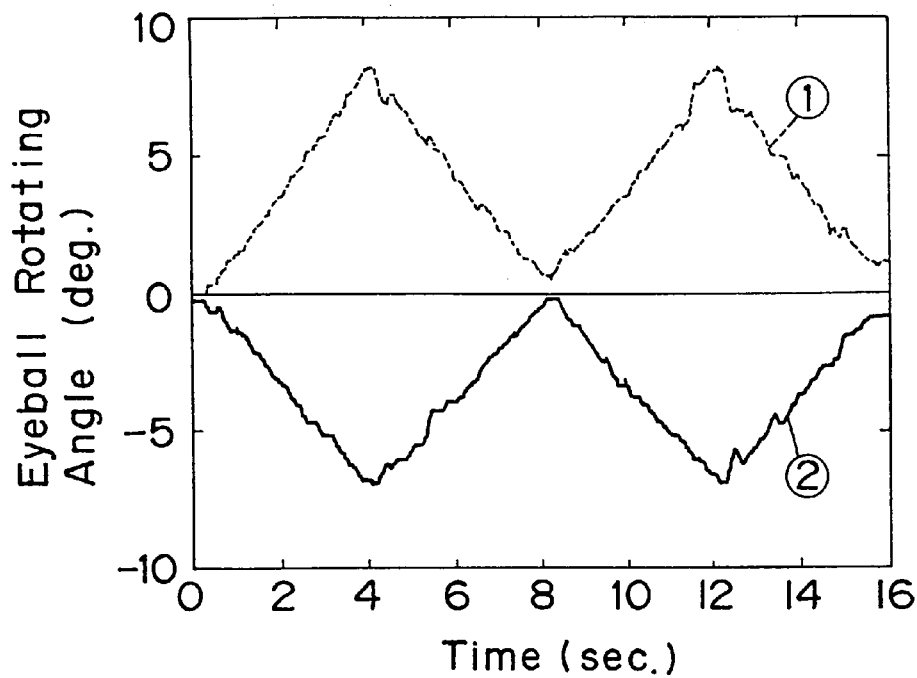
FIG. 11A is a diagram of the rotating angle of the eyeball that carries out convergence motion.
Figure 11B:
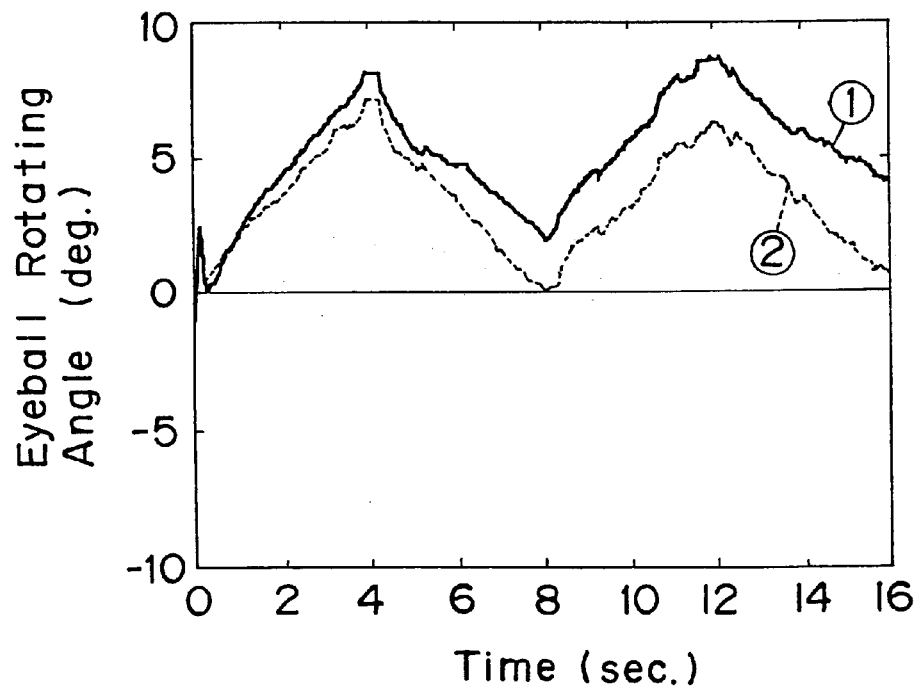
FIG. 11B is a diagram of the rotating angle of the eyeball that does not carry out convergence motion.

The eye movements can be evaluated by the changes of the eyeball rotating angle with time when fusion A position is moved back and forth. FIG. 11A is a drawing showing changes of the eyeball rotating angle with time of the eyeball that carries out convergence movements. On the other hand, FIG. 11B is a drawing showing changes of the eyeball rotating angle with time of the eyeball that does not carry out convergence movements. In each drawing, the elapsed time is taken as abscissa and the eyeball rotating angle as ordinate. The case when the eyeball moves in the right direction is designated as positive and the case when it moves in the left direction is designated as negative. The time point at time 0 is time when the stimulus convergence angle is 0 degree. In addition, numeral ① in the drawing shows the left eyeball rotating angle and numeral ② the right eyeball rotating angle. In the example shown in FIG. 11A, the right and left eyeballs are making convergence movements in accord with the shift of the subject point. That is, in such event, the images on both right and left eyes are fused and stereoscopic vision is achieved. On the other hand in the example shown in FIG. 11B, right and left eyeballs are not carrying out convergence movements but conjugate eyeball movements in which the right eye follows the left eye movements. In such event, the images on both right and left eyes are not fused. That is, no stereoscopic vision is achieved.

Based on this fact, the pupillary center position of both eyeballs of the subject is measured by imaging unit 20 (FIG. 2), and based on the measurement results, stereoscopic vision capacity of the subject can be automatically measured by deducing the indexes concerning the stereoscopic vision capacity by visual index calculating unit 16. For the indexes concerning the stereoscopic vision capacity, presence of convergence movements or conjugate eyeball movements, size of the eyeball rotating angle, pursuit gain which indicates ability of the eye movement by calculating the ratio of position or velocity for the eye movement to those for the moving stimulus, etc. can be utilized.

In the brain function examining apparatus according to Embodiment 3, pupillary index calculating unit 4 deduces the pupillary indexes and at the same time, visual index calculating unit 16 deduces the visual indexes concerning stereoscopic vision capacity. The index data of the relevant subject and the index data of a plurality of subjects measured in advance and stored in the database are outputted for enabling the comparison judgment. Thus, the brain functions can be examined, and as compared to the case in which the brain functions are examined from the pupillary index concerning the autonomic nervous system only, the statistical significant level value between the healthy normal elderly group and the dementia elderly group is further decreased, the identification rate or sensitivity of dementia cases can be improved, and furthermore, the degree of senescence of brain can be determined more accurately.

When the stereoacuity is examined, if the similar color as the background screen is used for the fusion, latency of the saccadic eye movement and/or variance of the fixation can also be examined simultaneously stereoacuity. For example, when the color of the background screen is blue, the color of the fusion arranged at the screen center should be slightly paler blue than that of the background screen. Thus, the identification rate of the dementia cases can be further improved, and in addition, the degree of senescence of brain can be judged more accurately. In addition, the brightness difference may be provided for the brightness of the fusion located at the screen center and the brightness of the background screen. Accordingly, when the stereoacuity is examined, the brightness difference identification capacity can also be examined, and the identification ratio or sensitivity of dementia cases can be further improved and the degree of senescence of brain can be judged more accurately.

(Embodiment 4)

For one of the visual system functions, there is a brightness difference identification capacity for identifying the brightness difference. In Reference 1 mentioned above, it is reported that there is a statistically significant capacity difference in brightness difference identification capacity between the Alzheimer type dementia group and the healthy normal group (p=0.01). Therefore, in Embodiment 4, the indexes concerning the visual system functions will be deduced by carrying out the visual examination concerning brightness difference identification capacity for identifying the brightness difference in the brain function examining apparatus according to Embodiment 1 or 2. In Embodiment 4, both brain function examining apparatus 10 (FIG. 2) and brain function examining apparatus 80 (FIG. 8) can be used. In the following description, brain function examining apparatus 10 (FIG. 2) is used. What differs is the kind of indexes concerning the visual system functions and there is no difference in calculating the pupillary indexes by the pupillary index calculating unit 4 (FIG. 2) and displaying the pupillary indexes and visual indexes.

Figure 12A:
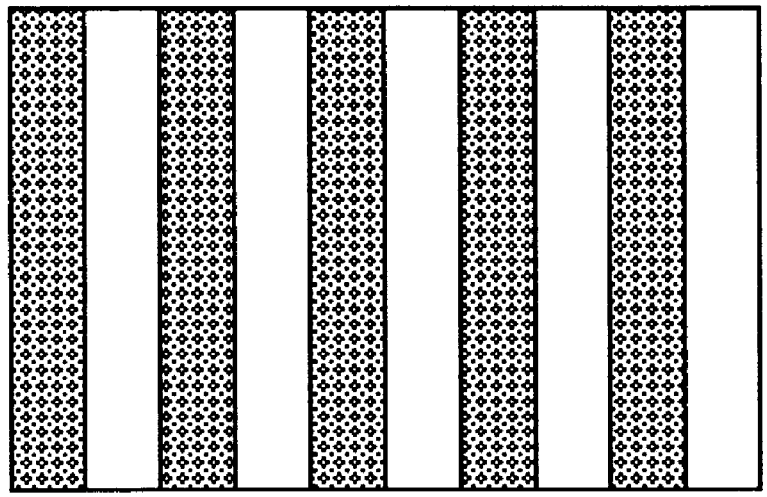
FIG. 12A is a diagram of an example of image for examination.
Figure 12B:
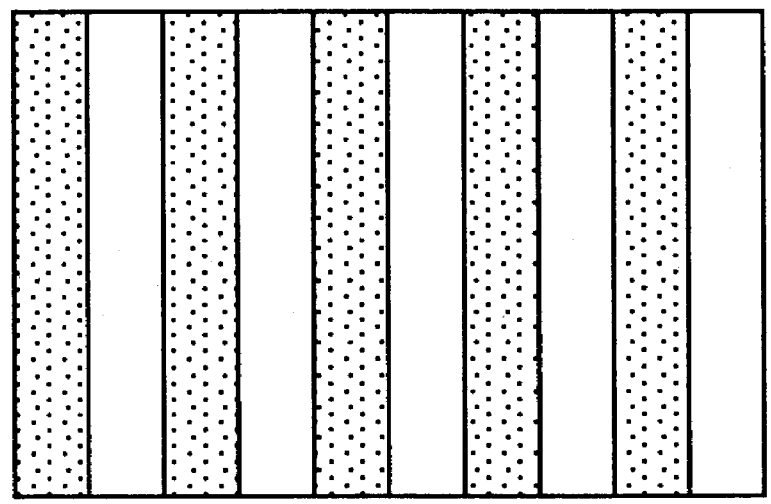
FIG. 12B is a diagram of an example of image for examination.

When the visual system functions are examined as described above, image generator 12 (FIG. 2) presents the image for examination to the subject by the use of image display unit 23 (FIG. 2). FIG. 12A is a drawing showing an example of the image for examination. FIGS. 12A and 12B are the striped images in which the areas with greater brightness and darker brightness appear alternately.

Image display unit 23 (FIG. 2) displays the completely white image and the striped image shown in FIG. 12A separately. The display is random. The test personnel presents a task to the subject to "Operate input unit 15 when you see the striped pattern." Operating input unit 15 (FIG. 2) when the subject recognizes the striped pattern causes visual index calculating unit 16 to deduce the visual indexes on the basis of the contents of the visual system function examination entered from control 11 and the information entered by the subject using input unit 15. Note that visual index calculating unit 16 can deduce the visual indexes without using input unit 15. As similar to Embodiment 1, the subject can enter his answers by looking at the recognized striped pattern.

When the brightness difference is able to be identified, the same examination is continually carried out by the use of the image of FIG. 12B. When the darker brightness areas of FIG. 12A and FIG. 12B are compared, it is understood that FIG. 12B is slightly brighter. If the subject is unable to identify the brightness difference, for example, the brightness difference in the image should be deduced as the visual index.

In this way, in the brain function examining apparatus according to Embodiment 4, the pupillary index is deduced at pupillary index calculating unit 4 and at the same time the visual index concerning the brightness difference identifying capacity is deduced at visual index calculating unit 16. The index data of the relevant subject and the index data of a plurality of subjects measured in advance and accumulated in the database are outputted for comparison and determination. Accordingly, the brain functions can be examined and as compared with the case in which the brain functions are examined by the pupillary index concerning the autonomic nervous system alone, the statistical significance level between the health normal elderly group and dementia case elderly group becomes smaller, the identification ratio or sensitivity of the dementia case is improved, and furthermore, the degree of senescence of the brain can be determined more accurately.

(Embodiment 5)

For one of the visual system functions, there is a capacity for tracing the moving object. In Reference 2 mentioned above, it is reported that there is a statistically significant capacity difference in pursuing capacity between the Alzheimer type dementia group and the healthy normal group (p=0.001). Therefore, in Embodiment 5, the indexes concerning the visual system functions will be deduced by carrying out the visual examination concerning tracing capacity for tracing objects in the brain function examining apparatus according to Embodiment 1 or 2. In Embodiment 5, both brain function examining apparatus 10 (FIG. 2) and brain function examining apparatus 80 (FIG. 8) can be used. In the following description, the brain function examining apparatus 10 (FIG. 2) is used. What differs is the kind of indexes concerning the visual system functions and there is no difference in calculating the pupillary indexes by pupillary index calculating unit 4 (FIG. 2) and displaying the pupillary indexes and visual indexes.

Figure 13:
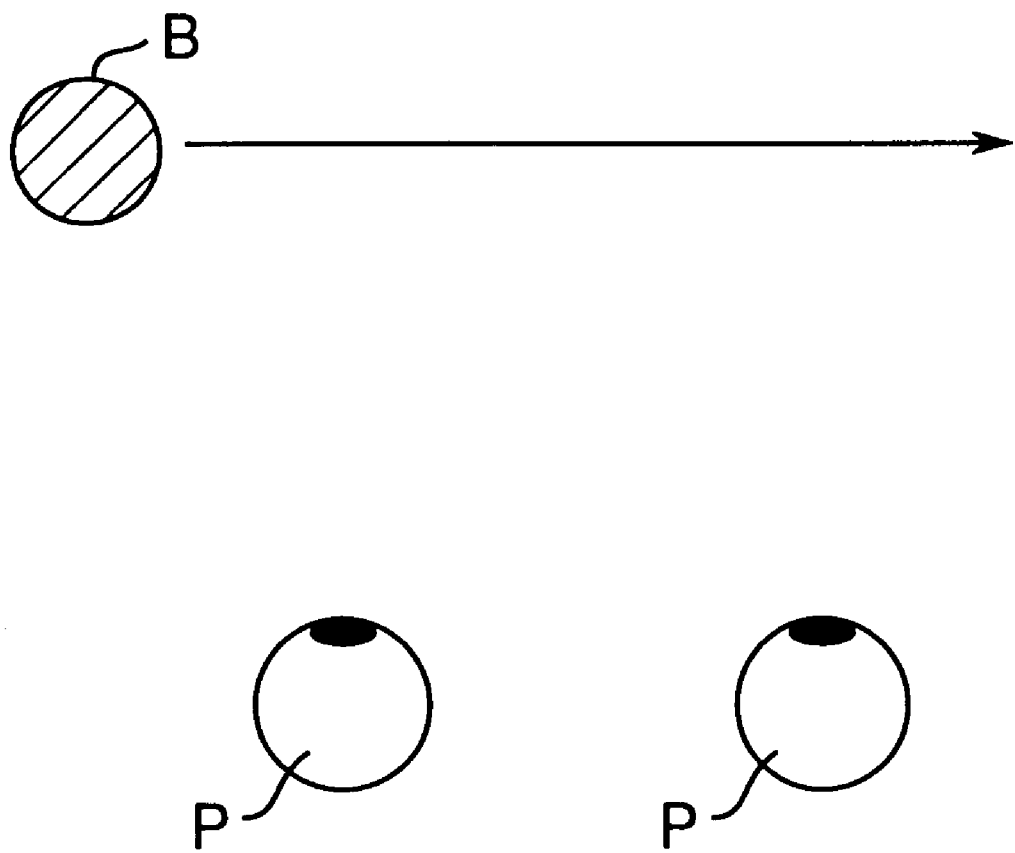
FIG. 13 is a diagram of an example of image for examination.

When the visual system functions are examined as described above, image generator 12 (FIG. 2) presents the image for examination to the subject by the use of image display unit 23 (FIG. 2). FIG. 13 is a drawing showing an example of the image for examination. For convenience of description, two eyeballs P are shown. Image display unit 23 (FIG. 2) displays a round target B of an image at the left end of the background screen and at the same time moves target B from left to right at a specified velocity. Note that the wording "a specified velocity" may be a fixed speed or a speed which varies in process of time expressed as a sine-wave form, for example. In such event, the subject's head is fixed to prevent moving and the subject is instructed to trace target B with eyes only. The motion of subject's eyeball P is measured by the image processing unit 3 (FIG. 2) by processing images imaged by the CCD camera 28 (FIG. 2). However, the measurement is also possible by the Electrooculography using, for example, the Ag—AgCl electrode.

Figure 19:
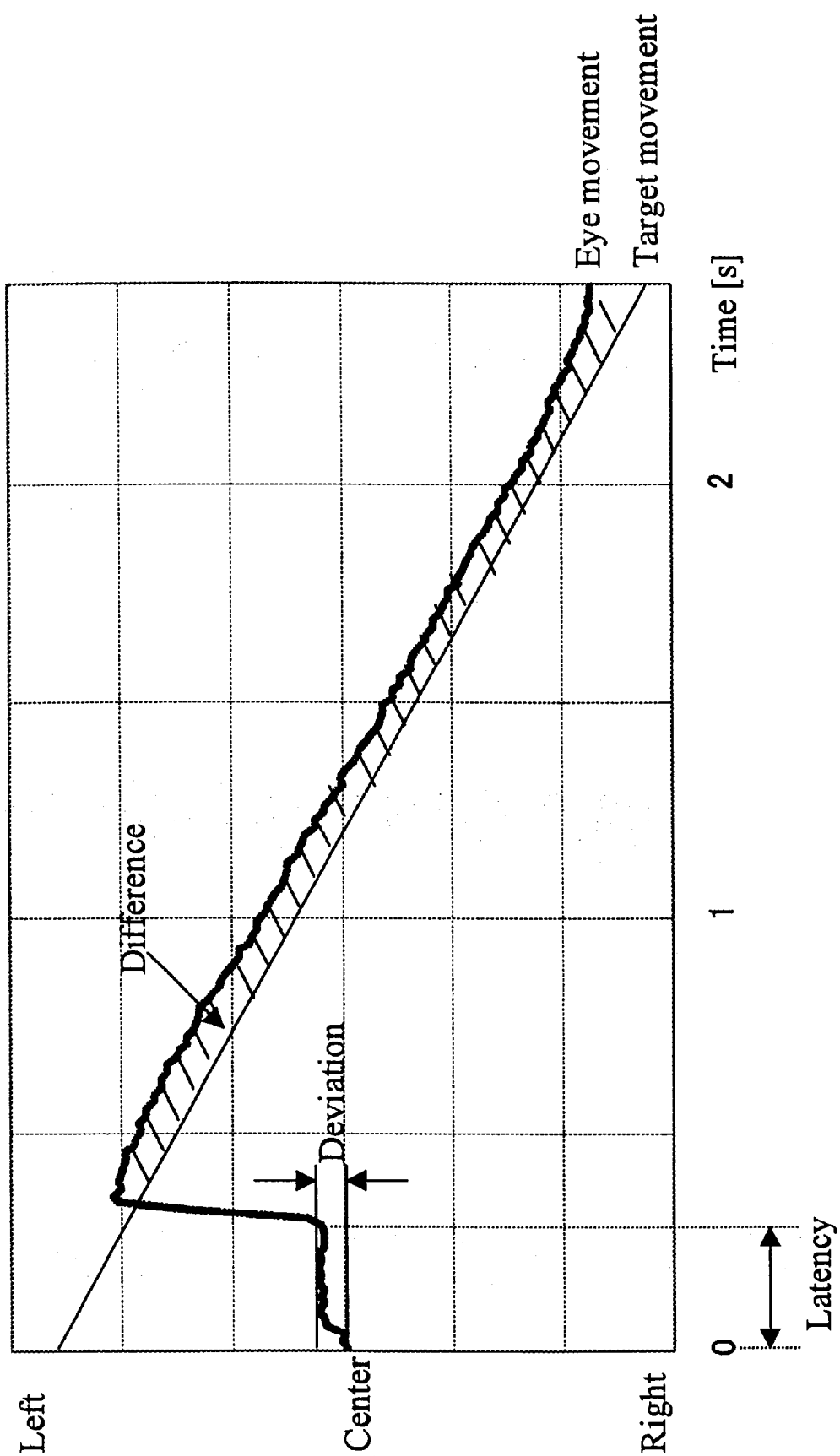
FIG. 19 a diagram which shows changes of a rotating angle of the eyeball tracking the target.

FIG. 19 is a diagram which shows changes of a rotating angle of the eyeball tracking the target. The target moves successively from left to right direction. In FIG. 19, time is taken as abscissa and the eyeball rotating angle and position of the target as ordinate. As seen from FIG. 19, smooth pursuit eye movement which is successive eye movement emerges. Smooth pursuit eye movement shows that eyeballs of the subject exactly tracks the target, since the subject can not give rise to smooth pursuit eye movement intentionally without presence of the target. Thus, emergence of the smooth pursuit eye movement can be considered that the eyeballs track the target.

More specifically, the target appears at 0 second. After a short latency of time, the eyeballs respond to and then keep tracking the target. Note that the subject is initially instructed to fix his eyeballs to a center of the blank area, at the time of which somewhat of deviation of the eyeballs can be observed as shown in FIG. 19. Further, differences between positions of the eyeballs and those of the target can also be observed in the figure and can be quantified as errors. Generally, the faster the target moves, the more the errors are prone to increase. Thus, the errors can be considered as a quantitative index for ability evaluation of target tracking, which is also represented as gains.

Figure 20:
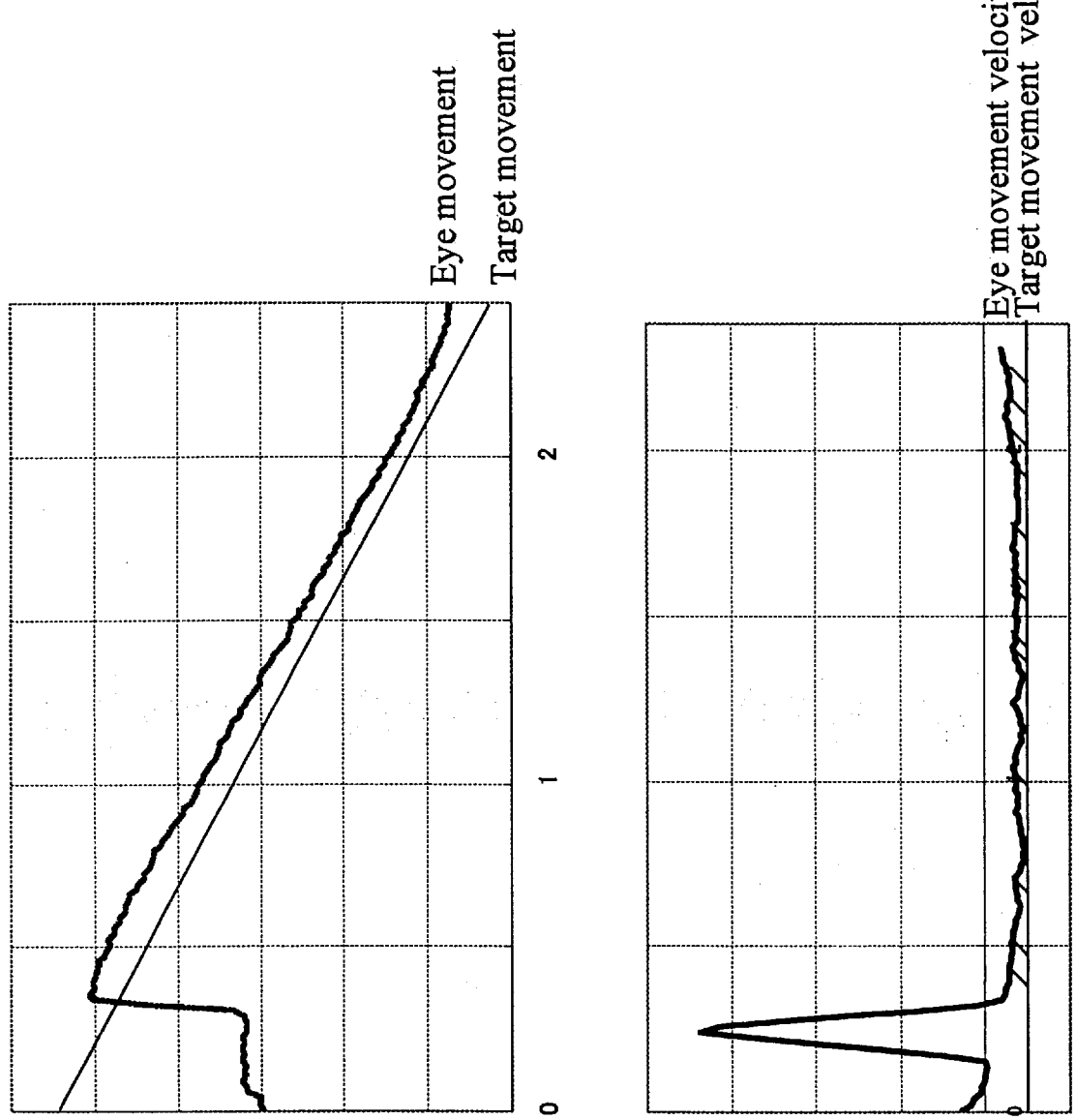
FIG. 20 is a diagram which shows relationship between eye/target movement and its velocity.

FIG. 20 is a diagram showing relationship between eye/target movement and its velocity. The upside diagram shows changes of a rotating angle of the eyeball tracking the target. The underside diagram shows changes of rotating angular velocity of the eyeball corresponding to the upside diagram. In the underside diagram, a steep peak can be found In the leftward, which means an abrupt change of angular velocity in transition from fixation of the eyeballs to smooth pursuit eye movement. It should be noted that there are some differences between the eye movement angular velocity and the target movement velocity similar to the eyeball rotating angle, which can be quantified as errors.

Figure 21:
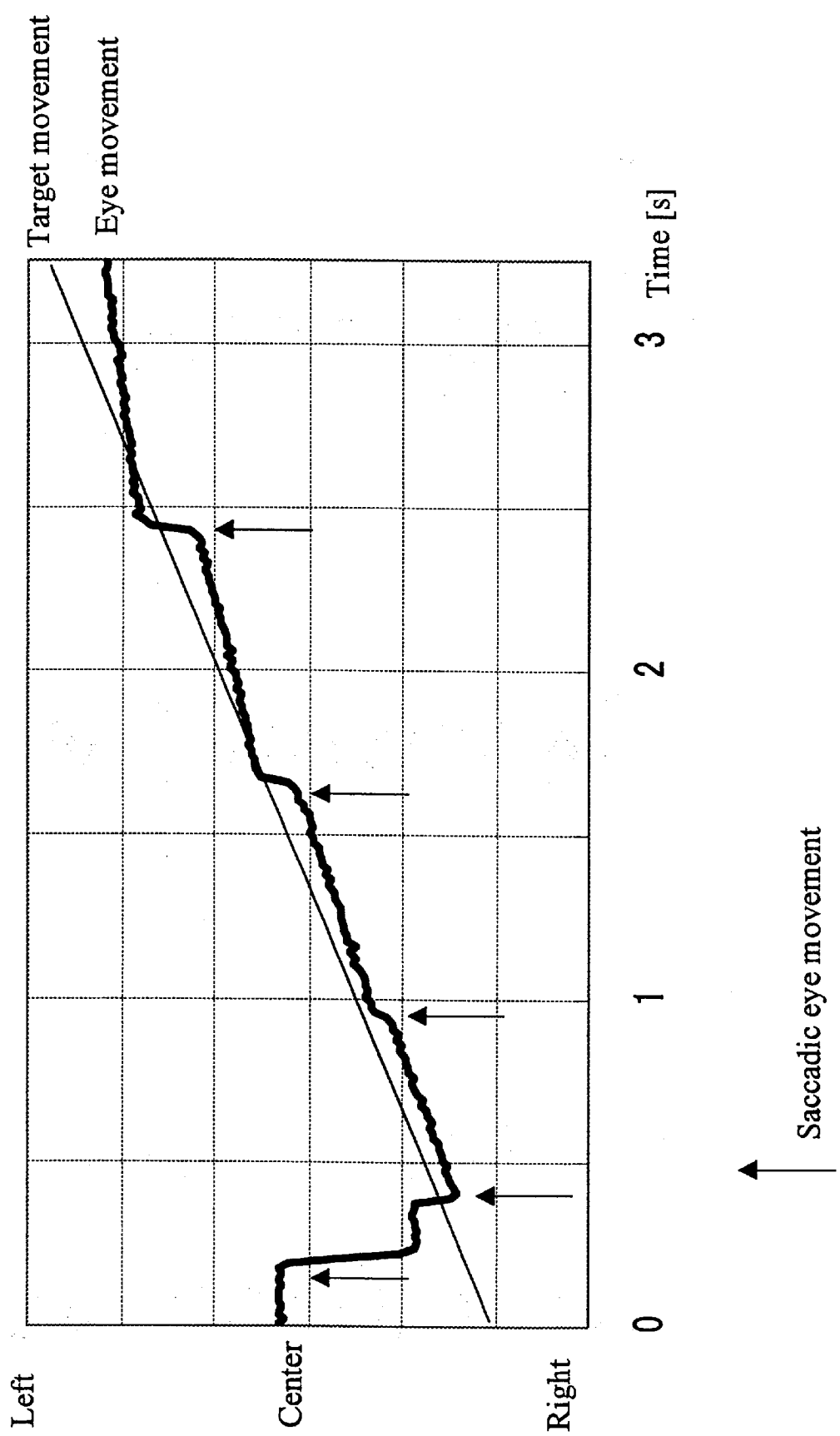
FIG. 21 is an exemplary diagram which shows changes of a rotating angle of another subject's eyeball, which tracking the target.

FIG. 21 is an exemplary diagram which shows changes of a rotating angle of another subject's eyeball, which tracking the target. As indicated by arrows in FIG. 21, the eyeballs of this subject performs discontinuous eye movement in smooth pursuit eye movement, which is referred to as saccadic eye movement and is the same type of eye movement emerged in reading a book. Numbers of saccadic eye movement in one measurement procedure can also be quantified, which shows frequencies of interruption of target-tracking and can be considered as a quantitative index for ability evaluation of smooth pursuit eye movement. In addition, saccadic amplitude, which is a displacement of a rotating angle resulted from saccadic eye movement, in one measurement procedure can be aggregated to be a quantitative index for ability evaluation of smooth pursuit eye movement.

As a result of measurement, visual index calculating unit 16 deduces the visual indexes concerning the tracing capacity. Specific examples of the visual index concerning tracing capacity include the traceable moving speed of target B in an image, maximum tracing speed of the tracing speed of the eyeball P with respect to each moving speed, the total sum of number of saccades and amplitude values, eye movement latency time, and ratio of the moving speed of target B in the image to tracing speed of eyeball P. Note that "saccade" means a rapid eyeball motion observed when the gazing point is changed to see voluntarily the object. It is known that once the motion occurs, it is unable to stop the motion voluntarily. Eye movement latency time refers to a length of time required for the eyes to start moving after target B appears and moves in the image.

In this way, in the brain function examining apparatus according to Embodiment 5, the pupillary indexes are deduced at the pupillary index calculating unit 4. The visual indexes concerning the object tracing capacity are deduced at the visual index calculating unit 16. The index data of the relevant subject and the index data of a plurality of subjects measured in advance and accumulated in the database are outputted for comparison and determination. Accordingly, the brain functions can be examined and as compared with the case in which the brain functions are examined by the pupillary index concerning the autonomic nervous system alone, the statistical significance level between the health normal elderly group and dementia case elderly group becomes smaller, the identification ratio or sensitivity of the dementia case is improved, and furthermore, the degree of senescence of the brain can be determined more accurately.

If color of target B is made quite similar to the color of the background screen when the object tracing capacity is examined, it is possible to carry out the color identification capacity simultaneously with the tracing capacity examination. For example, the background screen color is blue and the target B color should be slightly paler blue than that of the background screen. Thus, the identification rate of dementia cases is further improved and the degree of brain senescence can be more accurately determined. In addition, brightness difference is given to target B brightness and the background screen brightness. Thus, the brightness difference identification capacity can be also simultaneously examined, and the identification rate of dementia cases is further improved and the degree of brain senescence can be more accurately determined.

(Embodiment 6)

For one of the visual system functions, there is a capacity for identifying the original object based on the image of the object such as characters, patterns, etc., part of which is masked. In Reference 1 mentioned above, it is reported that there is a statistically significant capacity difference in the said capacity between the Alzheimer type dementia group and the healthy normal group (p=0.01). Therefore, in Embodiment 6, the indexes concerning the visual system functions will be deduced by carrying out the visual examination concerning the capacity for identifying the original object based on the masked object. For the brain function examining apparatus according to Embodiment 6, both brain function examining apparatus 10 (FIG. 2) and brain function examining apparatus 80 (FIG. 8) can be used. In the following description, brain function examining apparatus 10 (FIG. 2) is used. What differs is the kind of indexes concerning the visual system functions and there is no difference in calculating the pupillary indexes by pupillary index calculating unit 4 (FIG. 2) and displaying the pupillary indexes and visual indexes.

Figure 14A:
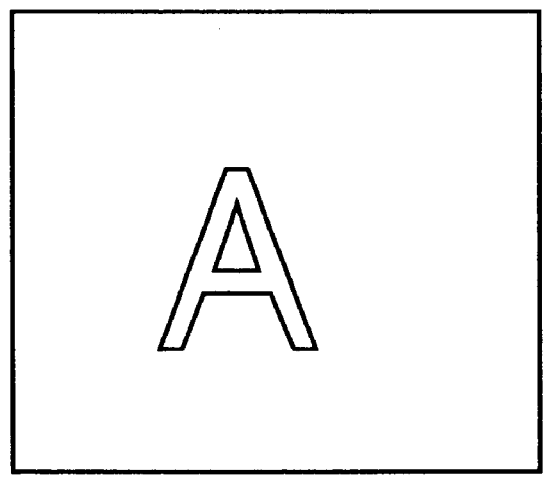
FIG. 14A is a diagram of an example of image for examination.
Figure 14B:
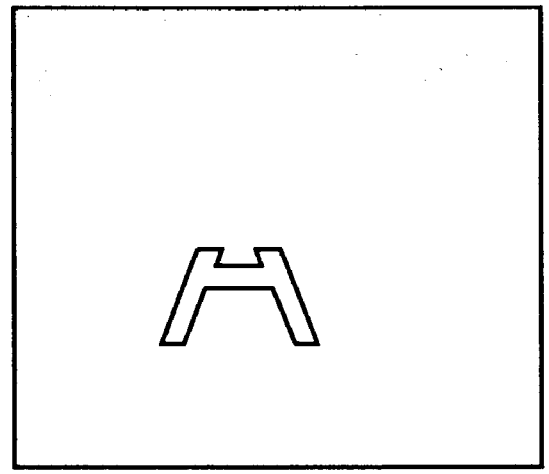
FIG. 14B is a diagram of an example of image for examination.
Figure 14C:
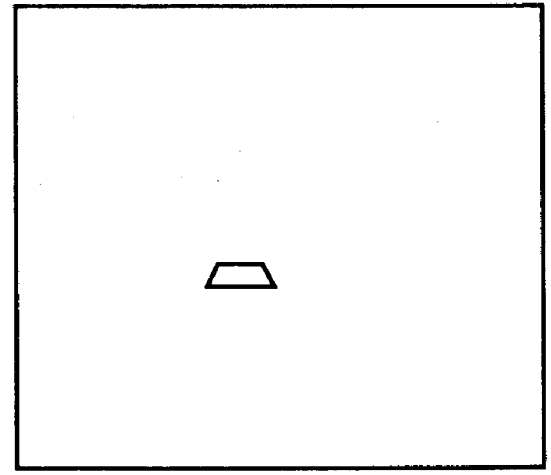
FIG. 14C is a diagram of an example of image for examination.

When the visual system functions are examined as described above, image generator 12 (FIG. 2) presents the image for examination to the subject by the use of image display unit 23. FIGS. 14A, 14B, and 14C are drawings showing examples of the image for examination. First of all, as shown in FIG. 14A, an image in which a letter "A" is disposed at the screen center is displayed to the subject in a very short time. The time for displaying the original letter is varied randomly between, for example, 16.7 msec and 300 msec. The shorter the display time of the original letter, the more difficult is to identify the original letter. Thereafter, as shown in FIG. 14B, the image with the top portion of letter "A" is masked or as shown in FIG. 14C, the image with all the portion other than the portion of horizontal bar of letter "A" masked is displayed to the subject for a specified time (for example, 100 msec).

The subject enters what the original letter is by the use of input unit 15 (FIG. 2). Visual index calculating unit 16 deduces the visual indexes based on the contents of the visual system functions examination entered from control section 11 and the information entered by the subject using input unit 15. Visual index calculating unit 16 evaluates the capacity based on the time when the original letter is being displayed. That is, if it is the right answer, it is evaluated that the shorter the display time, the higher is the capacity. Note that the input unit 15 is, for example, a joystick, and the original letter is entered by choosing the original letter "A" from a plurality of letters displayed at output unit 8 using the joystick. Or the keyboard may be used to enter the answer.

In this way, in the brain function examining apparatus according to Embodiment 6, the pupillary index is deduced at pupillary index calculating unit 4 and at the same time the visual index concerning the capacity for identifying the original object from the image of object whose part is masked is deduced at visual index calculating unit 16. The index data of the relevant subject and the index data of a plurality of subjects measured in advance and accumulated in the database are outputted for comparison and determination. Accordingly, the brain functions can be examined and as compared with the case in which the brain functions are examined by the pupillary index concerning the autonomic nervous system alone, the statistical significance level between the health normal elderly group and dementia case elderly group becomes smaller, the identification ratio or sensitivity of the dementia case is improved, and furthermore, the degree of senescence of the brain can be determined more accurately.

(Embodiment 7)

For one of the visual system functions, there is a capacity for identifying the object with the position displaced in a specified amount in a specified direction from a plurality of objects whose positions on the screen vary irregularly at specified time intervals. In Reference 3 mentioned above, it is reported that there is a statistically significant capacity difference in the said capacity between the Alzheimer type dementia group and the healthy normal group (p=0.001). Therefore, in Embodiment 7, the indexes concerning the visual system functions will be deduced by carrying out the visual examination concerning the capacity for identifying the object with the position displaced in a specified amount in a specified direction from a plurality of objects (for example, dots) whose positions on the screen vary irregularly at specified time intervals. In Embodiment 7, both brain function examining apparatus 10 (FIG. 2) and brain function examining apparatus 80 (FIG. 8) can be used. In the following description, brain function examining apparatus 10 (FIG. 2) is used. What differs is the kind of indexes concerning the visual system functions and there is no difference in calculating the pupillary indexes by pupillary index calculating unit 4 (FIG. 2) and displaying the pupillary indexes and visual indexes.

Figure 15A:
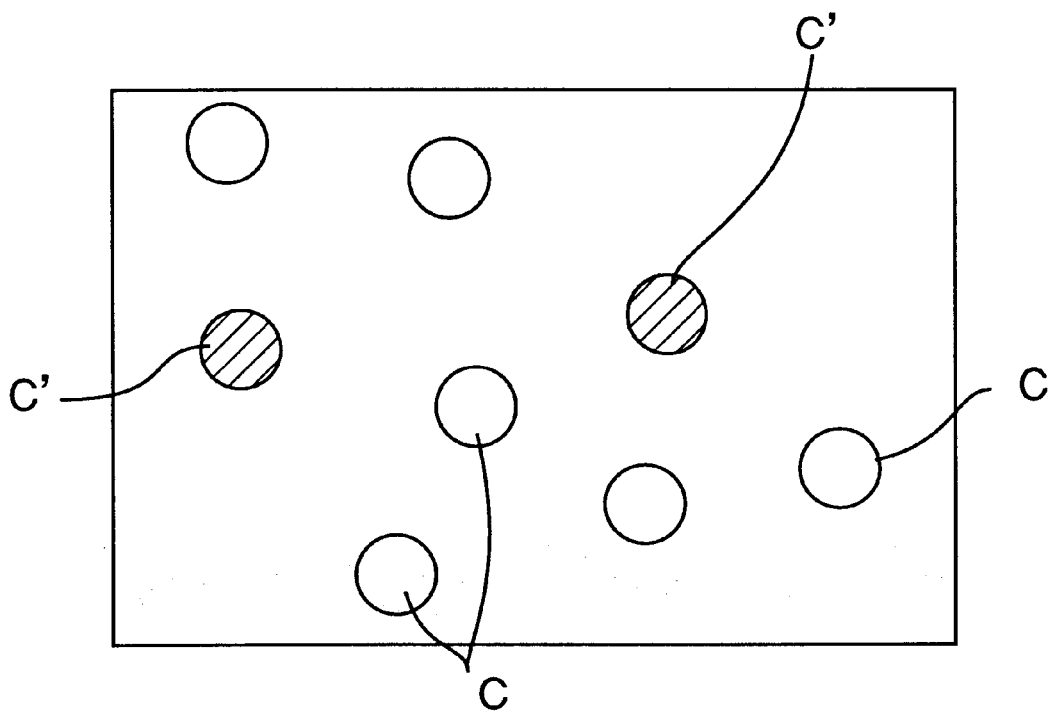
FIG. 15A is a diagram of an example of image for examination.
Figure 15B:
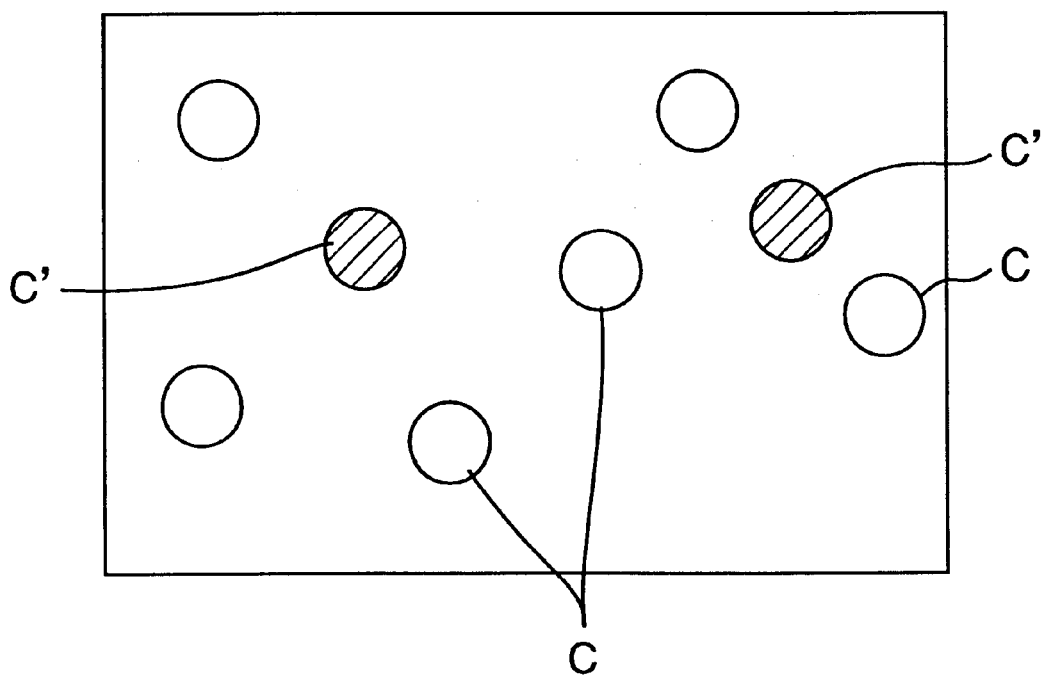
FIG. 15B is a diagram of an example of image for examination.

When the visual system functions are examined as described above, image generator 12 (FIG. 2) presents the image for examination to the subject by the use of image display unit 23. FIGS. 15A and 15B are drawings showing examples of the image for examination. As shown in FIG. 15A, an image in which a plurality of round objects (hereinafter called "dots") disposed at optional positions on the background screen is displayed to the subject. After a specified time is elapsed, as shown in FIG. 15B, the image with the position of dot C irregularly varied is displaced to the subject. Now, in the examination image shown in FIG. 15B, some of a plurality of dots C are displaced at a specified amount in the specified direction from the position shown in FIG. 15A. Dots C displaced in this way are called coherent dots C'. It is noted that in FIGS. 15A and 15B, coherent dots C' are hatched and other dots (called random dots) are shown in white circles. However, in the examination image, all the dots are displayed in the same color and same brightness, and dots C and coherent dots C' are unable to be identified only by their appearance.

The subject identifies coherent dots C' from the examination image (FIG. 15B) displayed by image display unit 23 and enters the direction in which coherent dots C' move using input unit 15 such as a joystick. If the subject is instructed to pursuit one of the coherent dots by his/her eyes as soon as he/she notices the direction of the coherent dots, the direction can be automatically specified even without using a joystick. Because the smooth pursuit eye movement cannot occur voluntarily without a continuously moving visual target. Visual index calculating unit 16 deduces the visual indexes based on the contents of the visual system functions examination entered from control section 11 and the information entered by the subject using input unit 15. Visual index calculating unit 16 evaluates the identifying capacity of the subject based on the ratio of coherent dots C' whose moving direction can be identified. That is, visual index calculating unit 16 evaluates that the shorter the time required for correctly entering the moving direction of coherent dots C', the higher is the identifying capacity of the subject.

Figure 16:
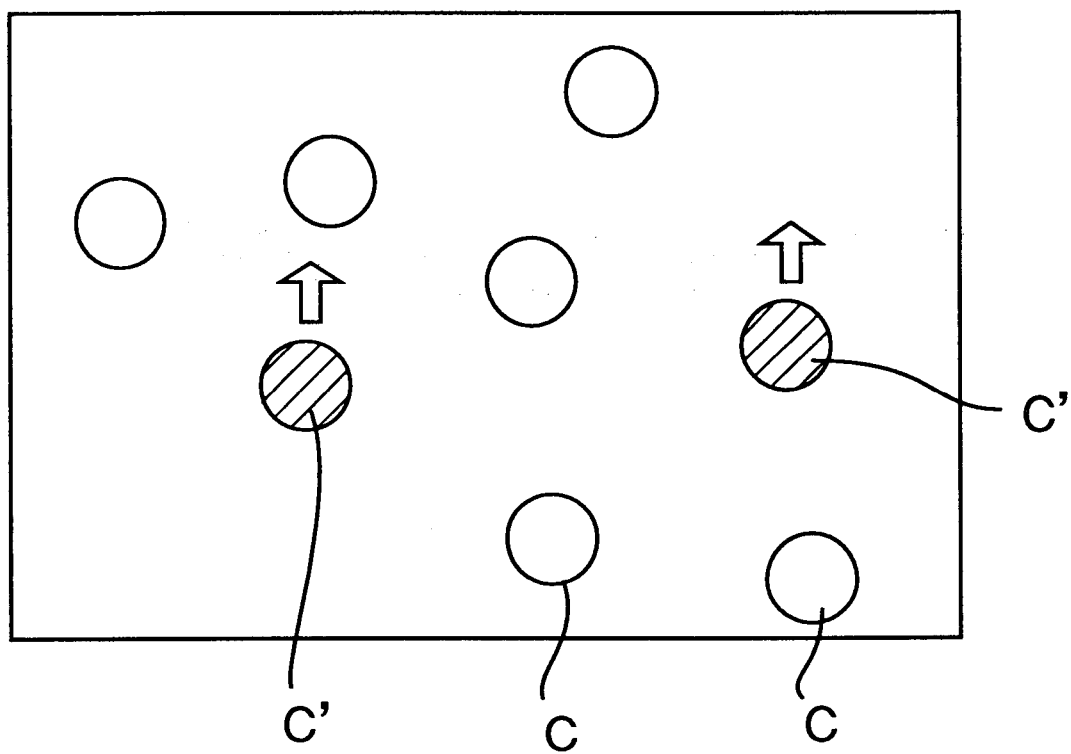
FIG. 16 is a diagram of another example of image for examination.

Note that it may be intended to randomly choose coherent dots C' from a plurality of dots C each time when image display unit 23 switches the examination image. However, as shown in FIG. 16, while one brain function examination is being carried out, the same dot is designated as coherent dot C' and this coherent dot C' may be moved at a specified amount in a specified direction at specified time intervals. By doing this, since the subject's eyeball moves in accordance with the direction to which coherent dot C' moves, the subject's identification capacity can be automatically measured by measuring the eyeball motion and the brain functions can be automatically determined.

Figure 22:
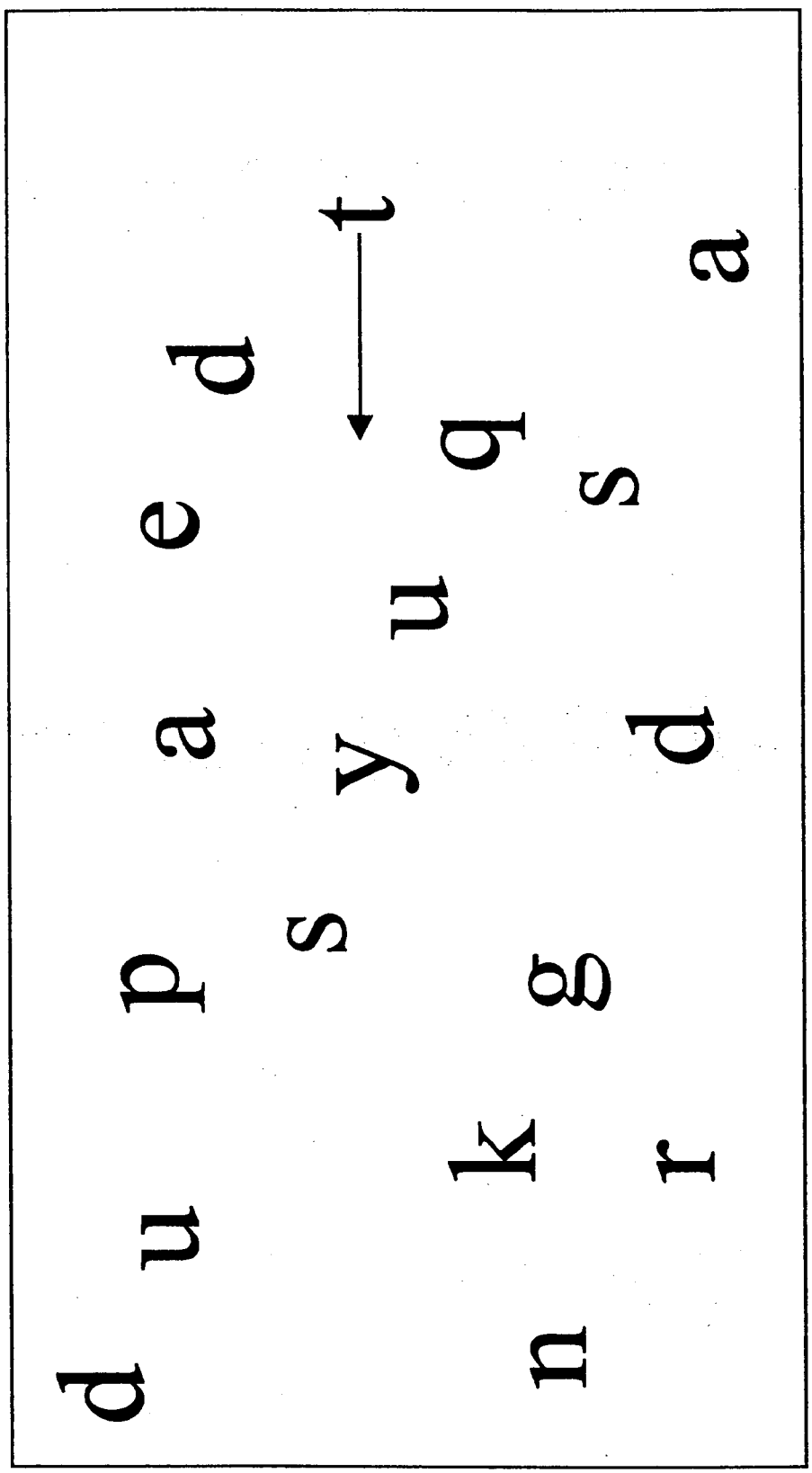
FIG. 22 is a diagram of an alternative example of the image for examination.

The visual stimulus for evaluating ability to perceive motions is not limited to dot patterns described above. FIG. 22 is a diagram of an alternative example of the image for examination. As shown in the figure, arbitrary characters are displayed in arbitrary positions. In this example, only one letter "t" moves successively from right to left direction. Each of all other letters is deleted and again displayed repeatedly in an arbitrary position and in an arbitrary cycle period, which is called as a distractor, since it disturbs successive movements of letter "t".

The test personnel presents a task to the subject, "Find and follow a successively moving letter in the display." A third party can readily judge whether the subject follows the successively moving letter or not objectively. This is because man can not give rise to smooth pursuit eye movement described in Embodiment 5 intentionally unless he looks at a successively moving target. Emergence of the smooth pursuit eye movement proves that the subject exactly looks at the target. On the other hand, emergence of the saccadic eye movement which means discontinuous eye movement represents that the subject has not looked at the target yet. Note that difficulty level of the task can be adjusted by changing the numbers of distractors.

Whether smooth pursuit eye movement emerges or not can be judged by the third party by observing movement of eyeballs. Alternatively, the judgement can be readily automated by recording the eye movement. By performing an automated judgement, quantitative values such as latency can be deduced so that ability of the subject to perceive motions can be evaluated quantitatively.

In this way, in the brain function examining apparatus according to Embodiment 7, the pupillary index is deduced at pupillary index calculating unit 4 and at the same time the visual index concerning the capacity for identifying the object with the position varied at a specified amount in the specified direction from a plurality of objects whose screen positions are irregularly varied at specified time intervals is deduced at visual index calculating unit 16. The index data of the relevant subject and the index data of a plurality of subjects measured in advance and accumulated in the database are outputted for comparison and determination. Accordingly, the brain functions can be examined and as compared with the case in which the brain functions are examined by the visual index concerning the autonomic nervous system alone, the statistical significance level between the health normal elderly group and dementia case elderly group becomes smaller, the identification ratio of the dementia case is improved, and furthermore, the degree of senescence of the brain can be determined more accurately.

Note that when image generator 12 displays the examination images shown in FIG. 15A and FIG. 15B, the colors of coherent dots and random dots are set to the color similar to the background screen, the color identification capacity can be simultaneously examined. For example, the background screen color is blue and the coherent dots and random dots colors should be slightly paler blue than that of the background screen. Thus, the identification rate of dementia cases is further improved and the degree of brain senescence can be more accurately determined. In addition, brightness difference is given to the coherent dots and random dots brightness and the background screen brightness. Thus, the brightness difference identification capacity can be also simultaneously examined when the coherent dot identification capacity is examined, and the identification rate of dementia cases is further improved and the degree of brain senescence can be more accurately determined.

From Embodiment 3 to Embodiment 7, examples of indexes concerning visual system functions are described in detail. Needless to say, indexes concerning visual system functions other than those can be adopted. They are briefly described as follows. These contents are described in detail in the specification and drawings of Japanese Patent Application No. 2001-232376 applied by the same assignee of the present application, whose contents are incorporated in the present specification for reference.

First of all, from a large number of letters or color patterns, the subject is instructed to find the specified letter or color pattern and to fix the eyes to the visual target after he finds the target. Based on the motion history of the subject's eyeball, the correct answer ratio, reaction time, gazing time, gazing frequency, gazing holding time, action time, etc. can be adopted as visual indexes. FIG. 23 is a exemplary diagram used for a task of searching letters. The test personnel presents a task to the subject to "Find and look at one character, which type is different from that of other characters. "5" in upper right portion of FIG. 23 is only a number, while the others are alphabetical letters. Although eyeballs of the subject frequently represent saccadic eye movement until he finds number "5", emergence of the saccadic eye movement stops because he looks at "5" after finding the number. Whether the task is completed or not can be judged objectively by determining the search to be executed when a time for looking at the letter exceeds a predetermined time length. The time length which the subject keeps looking at the letters is obtained by recording the eye movement. Perceptive searching ability can be evaluated quantitatively based on the time length to complete character search as an evaluation index.

In addition, an image showing prose is displayed before subject's eyes and the subject is instructed to read carefully the prose. Based on the motion history of the subject's eyeballs, the amount read for a specified time, forward saccade, reverse saccade, gazing holding time, etc. are able to be adopted as visual indexes.

Alternatively, on any of the four corners on the screen of the display device, the output unit 8 (FIG. 2), a round mark is displayed for a specified time (for example, 0.5 sec.) only. Based on the motion history of the subject's eyeballs when the subject gazes the round mark, the correct answer ratio, time lag, etc. can be adopted as visual indexes.

(Embodiment 8)

In Embodiment 8, the index of a type different from pupillary indexes and visual indexes described by now, that is, the index concerning the intelligence test carried out on the subject (intelligence evaluation index) will be described.

Figure 17:
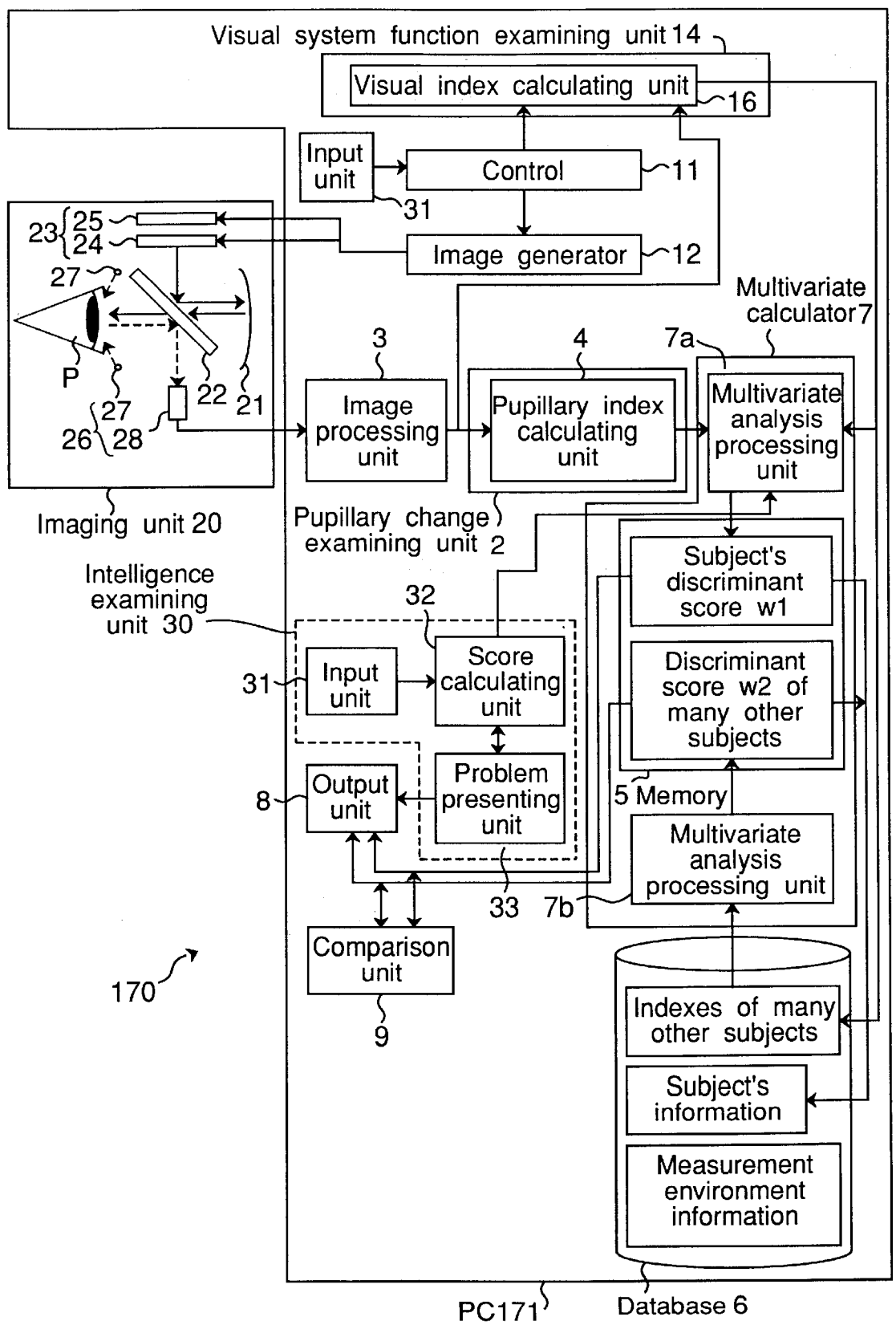
FIG. 17 is a block diagram of the configuration of the brain function examining apparatus according to Embodiment 8.

FIG. 17 is a block diagram showing the configuration of brain function examining apparatus 170 according to Embodiment 8. Brain function examining apparatus 170 is configured by adding an intelligence test unit 30 that carries out the intelligence test on the subject to brain function examining apparatus 80 (FIG. 8). Consequently, the description on the configuration same as that of brain function examining apparatus 80 (FIG. 8) will be omitted, and intelligence test unit 30 only will be described.

Intelligence test unit 30 carries out an intelligence test on the subject and deduces the intelligence evaluation index. Intelligence test unit 30 comprises an input unit 31, score calculating unit 32, and problem presenting unit 33. Examples of input unit 31 include a keyboard, mouse, speech input unit (not shown), etc. through which the subject enters answers. Score calculating unit 32 judges whether the entered answer is correct or not and calculates the score in accordance with the complexity of the problem and the answer. Score calculating unit 32 can be achieved by the calculation processing functions of PC171 represented by the central processing unit (CPU) (not shown). The score is calculated in conformity to the processing procedures of the computer program incorporated in advance. Problem presenting unit 33 displays the problem (question) prepared in advance on output unit 8. For example, "Where is the place we are in now?", "Say the answer one by one when 7 each is subtracted from 100.", "Tell the name of vegetables you know as many as possible." and the like. These problems may be stored in, for example, database 6 or in memory (not shown) which problem presenting unit 33.

Now, description will be made on the procedures of the intelligence test carried out by intelligence test unit 30. First of all, the problem presenting unit 33 displays the problem on the output unit 8. For example, the problem "Where is the place we are in now?" is displayed. The subject sees the displayed problem and enters the answer from the input unit 31. If no answer is given even after a specified time elapses (5 seconds) and it is judged that the subject is unable to voluntarily enter the answer, choices of the answer ("1. home; 2. hospital; 3. institution") can be displayed together. Based on the answer from the subject, the score calculating unit 32 calculates the score. For example, 2 points are given when the subject can voluntarily answer, 1 point when the subject chooses a correct answer from the choices, and 0 point for other cases. Thereafter, the problem presenting unit 33 continues to set a specified number of problems, receives the answers and calculates scores, respectively. Lastly, the total of the calculated scores is transmitted to multivariate analysis processing unit 7a of multivariate calculating unit 7. Multivariate analysis processing unit 7a utilizes the total score for calculating the discriminant score. This total score is the intelligent evaluation index.

As described above, the intelligent evaluation index is incorporated as one of the variables of the multivariate calculation and the discriminant score can be calculated. By combining indexes of different types such as pupillary indexes, visual indexes, and intelligence evaluating indexes, even when there is any bias due to individual difference, etc. in the specific type of index, it is possible to determine the brain functions more subjectively and highly reliably. Intelligence test unit 30 may be added to brain function examining apparatus 10 (FIG. 2). In such event, the output of score calculating unit 32 is directly outputted to the memory 5 (FIG. 2), and outputted to the output unit 8.

(Embodiment 9)

In Embodiment 9, the indexes of types different from pupillary indexes, visual indexes, and intelligent evaluating indexes, that is, the indexes concerning behavior evaluation examination (behavior evaluating index) for behaviors of the subject. The behavior evaluation is known as Clinical Dementia Rating (so-called CDR). For examination concerning these behavior evaluations, the behavior examining unit (not shown) same as the intelligence examining unit 30 should be installed.

The behavior evaluating indexes are indexes scored by the third party other than the subject (for example, care providers of the relevant subject) who answer the questions concerning the behaviors of the subject. For the questions, it would be appropriate to ask the matters which no one but care providers could answer, for example, "Does the subject remember that he/she has taken meals?", etc. This kind of questions are prepared in accord with categories such as eating behavior, clothes, interpersonal relation, etc. Questions may be set by a component element similar to the problem presenting unit 33 of the intelligent test unit 30 described in Embodiment 8, which is also provided for Embodiment 9. Alternatively, questions may be recited in paper questionnaires. In the former case, a score calculating unit should be further installed to the behavior examining section (not shown) and scores are automatically calculated. In the latter case, the test personnel, etc. must enter the score totaled from the questionnaire through input unit 31 of the behavior examining unit (not shown). The score referred to here is the behavior evaluating index. The behavior examining unit (not shown) transmits the score to the multivariate analysis processing unit 7a of multivariate calculating unit 7. Multivariate analysis processing unit 7a utilizes the score for calculating the discriminant score. Other configuration is same as, for example, the brain function examining apparatus 10 (FIG. 2).

As described above, the behavior evaluating index is incorporated as one of the variables of multivariate calculation and the discriminant score can be calculated. By combining different types of indexes such as pupillary indexes, visual indexes, and behavior evaluating indexes, even when there is any bias due to individual difference, etc. in the specific type of index, it is possible to determine the brain functions more subjectively and highly reliably.

The contents of Embodiments 8 and 9 are described in detail in the specification and drawings of Japanese Patent Application No. 2001-232378 applied by the same assignee of the present application, whose contents are incorporated in the present specification for reference.

As described above, the best preferred embodiments according to the present invention were described. In the present invention, four types of independent indexes (pupillary indexes, visual indexes, intelligence evaluating indexes, and behavior evaluating indexes) which indicate characteristics of brain functions are combined to examine brain functions. In Embodiments 1 through 0, combinations of specific indexes only are described, but combinations of these four types of indexes are optional. By combining independent indexes, as compared with the case in which the brain functions are examined by one type of index alone, the statistical significance level between the health normal elderly group and dementia case elderly group becomes smaller, the identification ratio of the dementia case is improved, and furthermore, the degree of senescence of the brain can be determined more accurately.

Furthermore, it is possible to further utilize the physiological examination indexes that indicate characteristics related to brain functions. The physiological examination indexes, for example, cerebrospinal fluid tau protein, beta amiloyd protein, or apolipoprotein E genotype are those indicating the characteristics of the organism of the subject, which are obtained, for example, by blood component analysis, cerebrospinal fluid analysis, etc. of the subject (Hiroyuki Arai et al., "Biological markers for the clinical diagnosis of Alzheimer's disease", Sinkei Kenkyu no Shinpo, Vol.41, No.1, pp.130–139, 1997). Entering the results of the physiological examination from the input unit and accumulating the physiological examination indexes of dementia case patients, etc. in database enables the grasping of characteristics of brain functions from the viewpoint of characteristics of the organism.

The processing operations of each component element that composes the brain function examining apparatus described in Embodiments 1 through 9 can be achieved as a computer program for allowing the computer to execute such processing. Such computer program is recorded in optical disks such as CD, DVD, etc., magnetic recording medium such as flexible discs, etc., and semiconductor recording medium such as flash memory, etc. In addition, such computer program is transmitted through network such s Internet, etc. as electric signals.

Although the present invention has been described in connection with the preferred embodiments thereof with reference to the accompanying drawings, it is to be noted that various changes and modifications will be apparent to those skilled in the art. Such changes and modifications are to be understood as included within the scope of the present invention as defined by the appended claims, unless they depart therefrom.

What is claimed is:

1. An apparatus which examines brain functions of a subject comprising:

two or more examining units of a pupillary change examining unit configured to examine characteristics of a pupil of the subject and to calculate a pupillary index, a visual system function examining unit configured to examine visual system functions of the subject and to calculate a visual index, an intelligence examining unit configured to carry out an intelligence test on the subject and to calculate an intelligence evaluating index, and a behavior examining unit configured to provide a behavior evaluating index that shows a result of a behavior test of the subject;

a memory device configured to store a plurality of indexes presented by the two or more examining units;

an output unit configured to output the plurality of indexes stored in the memory unit;

a database configured to accumulate a plurality of reference indexes each of which serves as a reference of each of the plurality of indexes; and a multivariate calculator configured to calculate at least one discriminant score in a quantity less than a number of input values based on a plurality of the input values;

wherein the output unit further outputs the plurality of reference indexes accumulated in the database, wherein the multivariate calculator calculates the at least one discriminant score using the plurality of indexes presented by the two or more examining units and the plurality of reference indexes accumulated in the database as the plurality of input values for calculating the at least one discriminant score, and wherein the discriminant score calculated by the multivariate calculator is used as a discriminant score for diagnosis of an Alzheimer-type dementia case.

2. The brain function examining apparatus according to claim 1, wherein the pupillary index concerns a pupillary size of the subject, the visual index concerns motions of eyeballs of the subject, the intelligence evaluating index concerns the intelligence test on the subject scored in accordance with first answers of the subject to first questions, and the behavior evaluating index concerns the behavior test of the subject scored in accordance with second answers of a third party different from the subject to second questions different from the first questions.

3. The brain function examining apparatus according to claim 2, wherein the visual index concerns at least one of capacities for identifying specific colors, for tracing a continuously moving target in an image, for tracing two kinds of images expressed by deviating the images by parallax of both eyes, for searching an image emerging at random in a visual field, for detecting a motion when some of elements of an image move, for identifying a specific element with respect to plural kinds of elements, and for reading and understanding when prose is carefully read.

4. The brain function examining apparatus according to claim 2, wherein the pupillary index related to light reflex is at least one of a natural pupillary diameter, latency of response, pupillary constricting time, pupillary redilation time, amplitude of pupillary constriction, pupil constricting rate, pupillary constricting velocity, pupillary redilating velocity, acceleration of pupillary constriction, time required to attain maximum velocity of pupillary constriction, time required to attain maximum velocity of pupillary redilation, and time required to attain maximum acceleration of pupillary constriction.

5. The brain function examining apparatus according to claim 2, wherein the visual index includes at least one of:

latency of eye fixation from a time when stimulus is given, number of eye fixations, an eye fixation time to gaze a visual target, latency of saccadic eye movement initiation from a time when stimulus is given, number of saccades, amplitude of saccade, peak velocity of smooth pursuit, gain of smooth pursuit eye movement which is a ratio of eye movement velocity of eye movement displacement to target velocity of target displacement, gain of smooth pursuit eye movement which is a ratio of accumulation of eye movement displacement to accumulation of target displacement, and binocular parallax.

6. The brain function examining apparatus according to claim 1, wherein the plurality of reference indexes are accumulated with at least one of ages of other subjects and disease names identified.

7. The brain function examining apparatus according to claim 1 further comprising a comparison unit configured to compare the plurality of indexes presented by the two or more examining units and the plurality of reference indexes accumulated in the database.

8. The brain function examining apparatus according to claim 1, wherein the plurality of indexes used as the plurality of input values are pupillary indexes concerning the pupillary size of the subject and at least one visual index concerning the motions of subject's eyeballs.

9. The brain function examining apparatus according to claim 8, wherein the plurality of indexes used as the plurality of input values are at least one of the intelligence evaluating index and the behavior evaluating index.

10. The brain function examining apparatus according to claim 1, wherein the plurality of indexes used as the plurality of input values are at least two of the pupillary index, visual index, the intelligence evaluating index and the behavior evaluating index.

11. The brain function examining apparatus according to claim 1, wherein the multivariate calculator carries out multivariate calculations by a discriminant analysis method.

12. The brain function examining apparatus according to claim 1, wherein the multivariate calculator carries out multivariate calculations using a neural network.

13. The brain function examining apparatus according to claim 1, wherein the multivariate calculator carries out multivariate calculations using an expert system.

14. The brain function examining apparatus according to claim 1 further comprising an imaging unit including:

a light source configured to irradiate the subject's pupil with light, a camera configured to image the pupil by the light irradiated from the light source and to generate and output a pupillary image data, and an image display unit configured to present an image, wherein the brain function examining apparatus further comprises an image processing unit configured to extract a pupillary size and a center of the pupil based on the pupillary image outputted by the camera, wherein the pupillary change examining unit comprises a pupillary index calculating unit configured to calculate pupillary indexes in accordance with the pupillary diameter based on the pupillary size and the center of the pupil extracted by the image processing unit, and wherein the visual system function examining unit comprises a visual index calculating unit configured to calculate visual indexes in accordance with the center of the pupil extracted by the image processing unit.

15. The brain function examining apparatus according to claim 14, wherein the imaging unit receives an image presented at the image display unit through a network and transmits the pupillary image generated by the camera through the network.

16. The brain function examining apparatus according to claim 1 further comprising an input unit configured to enter a physiological examining index that shows physiological characteristics of the subject.

17. The brain function examining apparatus according to claim 1, wherein the memory device stores the visual indexes presented by the visual system function examining unit, wherein the output unit outputs the visual indexes stored in the memory unit, and wherein the visual indexes concern motions of eyeballs of the subject and include at least two of capacities for identifying specific colors, for tracing a continuously moving target in an image, for tracing two kinds of images expressed by deviating the images by parallax of both eyes, for searching an image emerging at random in a visual field, for detecting a motion when some of elements of an image move, for identifying a specific element with respect to plural kinds of elements, and for reading and understanding when prose is carefully read.

18. A brain function examining system comprising a brain function examining apparatus according to claim 1 and a database server which are connected via a network, wherein the database server has another database configured to accumulate the plurality of reference indexes, and wherein the database server transmits the plurality of reference indexes accumulated in the another database to the brain function examining apparatus via the network and the output unit of the brain function examining apparatus further outputs the plurality of reference indexes transmitted from the database server.

19. The brain function examining system according to claim 18, wherein the brain function examining apparatus transmits the plurality of indexes to the database server, and the database server further includes a comparison unit configured to compare the plurality of indexes received from the brain function examining apparatus and the plurality of reference indexes accumulated in the another database, and outputs the comparison results of the comparison unit to the brain function examining apparatus via the network.

20. An apparatus which examines brain functions of a subject comprising:

two or more examining units of a pupillary change examining unit configured to examine characteristics of a pupil of the subject and to calculate a pupillary index, a visual system function examining unit configured to examine visual system functions of the subject and to calculate a visual index, an intelligence examining unit configured to carry out an intelligence test on the subject and to calculate an intelligence evaluating index, and a behavior examining unit configured to provide a behavior evaluating index that shows a result of behavior test of the subject;

a memory device configured to store a plurality of indexes presented by the two or more examining units;

an output unit configured to output the plurality of indexes stored in the memory unit;

a database configured to accumulate a plurality of reference indexes each of which serves as a reference of each of the plurality of indexes; and a multivariate calculator configured to calculate at least one discriminant score in a quantity less than a number of input values based on a plurality of the input values;

wherein the output unit further outputs the plurality of references indexes accumulated in the database, wherein the multivariate calculator calculates the at least one discriminant score using the plurality of indexes presented by the two or more examining units and the plurality of reference indexes accumulated in the database as the plurality of input values for calculating the at least one discriminant score, and wherein the multivariate calculator carries out multivariate calculations by a quadratic discrimination method.

21. An apparatus which examines brain functions of a subject comprising:

two or more examining units of a pupillary change examining unit configured to examine characteristics of a pupil of the subject and to calculate a pupillary index, a visual system function examining unit configured to examine visual system functions of the subject and to calculate a visual index, an intelligence examining unit configured to carry out an intelligence test on the subject and to calculate an intelligence evaluating index, and a behavior examining unit configured to provide a behavior evaluating index that shows a result of behavior test of the subject;

a memory device configured to store a plurality of indexes presented by the two or more examining units;

an output unit configured to output the plurality of indexes stored in the memory unit;

a database configured to accumulate a plurality of reference indexes each of which serves as a reference of each of the plurality of indexes; and a multivariate calculator configured to calculate at least one discriminant score in a quantity less than a number of input values based on a plurality of the input values;

wherein the output unit further outputs the plurality of references indexes accumulated in the database, wherein the multivariate calculator calculates the at least one discriminant score using the plurality of indexes presented by the two or more examining units and the plurality of reference indexes accumulated in the database as the plurality of input values for calculating the at least one discriminant score, and wherein the multivariate calculator carries out multivariate calculations using a fuzzy theory.

22. A brain function examining method which carries out examination of a subject's brain functions by use of a brain function examining apparatus comprising two or more examining units of a pupillary change examining unit configured to examine characteristics of a pupil of the subject and which calculates to calculate a pupillary index, a visual system function examining unit which examines configured to examine visual system functions of the subject and to calculate a visual index, an intelligence examining unit configured to carry out an intelligence test on the subject and to calculate an intelligence evaluating index, and a behavior examining unit configured to provide a behavior evaluating index that shows a result of a behavior test of the subject, the brain function examining apparatus further comprising:

a database configured to accumulate a plurality of reference indexes each of which serves as a reference of each of the plurality of indexes, and a multivariate calculator configured to calculate at least one discriminant score in a quantity less than a number of input values based on a plurality of the input values, the method comprising:
acquiring a plurality of indexes from the two or more of the examining units,
storing the plurality of indexes acquired, and
outputting the plurality of indexes stored,
wherein the multivariate calculator calculates the at least one discriminant score using the plurality of indexes presented by the two or more examining units and the plurality of reference indexes accumulated in the database as the plurality of input values for calculating the at least one discriminant score, and
wherein the discriminant score calculated by the multivariate calculator is used as a discriminant score for diagnosis of an Alzheimer-type dementia case.

23. The brain function examining method according to claim 22, further comprising:
storing the at least one calculated discriminant score; and
outputting the stored at least one discriminant score.

24. A recording medium for recording a computer-executable program operating a brain function examining apparatus comprising two or more examining units of
a pupillary change examining unit configured to examine characteristics of a pupil of the subject and to calculate a pupillary index,
a visual system function examining unit configured to examine visual system functions of the subject and which calculates to calculate a visual index,
an intelligence examining unit configured to carry out an intelligence test on the subject and which calculates to calculate an intelligence evaluating index, and
a behavior examining unit configured to provide a behavior evaluating index that shows a result of a behavior test of the subject, the brain function examining apparatus further comprising:
a database configured to accumulate a plurality of reference indexes each of which serves as a reference of each of the plurality of indexes, and
a multivariate calculator configured to calculate at least one discriminant score in a quantity less than a number of input values based on a plurality of the input values,
the program comprising:
acquiring a plurality of indexes from the two or more of the examining units,
storing the plurality of indexes acquired, and
outputting the plurality of indexes stored,
wherein the multivariate calculator calculates the at least one discriminant score using the plurality of indexes presented by the two or more examining units and the plurality of reference indexes accumulated in the database as the plurality of input values for calculating the at least one discriminant score, and
wherein the discriminant score calculated by the multivariate calculator is used as a discriminant score for diagnosis of an Alzheimer-type dementia case.

25. The recording medium for recording the computer-executable program according to claim 24, comprising:
storing the at least one calculated discriminant score; and
outputting the stored at least one discriminant score.

* * * * *

UNITED STATES PATENT AND TRADEMARK OFFICE
CERTIFICATE OF CORRECTION

PATENT NO.    : 6,702,757 B2
DATED         : March 9, 2004
INVENTOR(S)   : Shogo Fukushima et al.

It is certified that error appears in the above-identified patent and that said Letters Patent is hereby corrected as shown below:

<u>Title page,</u>
Item [57], ABSTRACT,
Line 5, please delete "the".
Line 7, please add -- of -- after "results".

<u>Column 16,</u>
Line 12, please replace "$x_{j1}$ and $y_{j1}$" with -- $x_{i1}$ and $y_{i1}$ --.
Line 26, please replace "$x_j$" with -- $x_i$ --.

<u>Column 28,</u>
Line 7, please replace "0" with -- 9 --.

<u>Column 32,</u>
Line 48, please delete "which".
Line 49, please delete "calculates".
Line 50, please delete "which examines".

<u>Column 33,</u>
Lines 30 and 32, please delete "which calculates".

Signed and Sealed this

Twentieth Day of July, 2004

JON W. DUDAS
*Acting Director of the United States Patent and Trademark Office*